US012746124B2

(12) United States Patent
Alavi et al.

(10) Patent No.: US 12,746,124 B2
(45) **Date of Patent: *Sep. 29, 2026**

(54) TRANSCATHETER VALVE SYSTEM AND METHOD FOR VENOUS INSUFFICIENCY

(71) Applicant: enVVeno Medical Corporation, Irvine, CA (US)

(72) Inventors: Hamed Alavi, Irvine, CA (US); Mevan L. Siriwardane, Irvine, CA (US); Tanya M. Hnatiw, Ontario, CA (US); Nicholas K. Williams, Santa Ana, CA (US)

(73) Assignee: enVVeno Medical Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/544,432

(22) Filed: Feb. 19, 2026

(65) Prior Publication Data

US 2026/0183114 A1 Jul. 2, 2026

Related U.S. Application Data

(63) Continuation of application No. 18/196,121, filed on May 11, 2023, now Pat. No. 12,575,932.

(60) Provisional application No. 63/404,150, filed on Sep. 6, 2022, provisional application No. 63/340,867, filed on May 11, 2022.

(51) Int. Cl.
*A61F 2/24* (2006.01)

(52) U.S. Cl.
CPC .......... *A61F 2/2475* (2013.01); *A61F 2/2415* (2013.01); *A61F 2/2418* (2013.01); *A61F 2/2433* (2013.01); *A61F 2220/0075* (2013.01); *A61F 2230/0069* (2013.01); *A61F 2250/0039* (2013.01)

(58) Field of Classification Search
CPC .................. A61F 2/2475; A61F 2/2415; A61F 2220/0075
See application file for complete search history.

(56) References Cited

U.S. PATENT DOCUMENTS 4,922,905 A 5/1990 Strecker
5,509,930 A * 4/1996 Love .................... A61F 2/2412 623/900

(Continued)

FOREIGN PATENT DOCUMENTS

EP 0183904 A2 6/1986
EP 2289466 A1 3/2011

(Continued)

OTHER PUBLICATIONS

International Application No. PCT/US2023/021849, International Filing Date May 11, 2023, International Search Report, dated Jul. 11, 2023.

(Continued)

*Primary Examiner* — Javier G Blanco
(74) *Attorney, Agent, or Firm* — Herbert Smith Freehills Kramer (US) LLP

(57) ABSTRACT

This application generally relates to an transcatheter anti-reflux venous valve endoprosthesis system, including a replacement valve, a valve support frame, crimping system, and delivery system to treat patients with chronic venous insufficiency, and method for using such a system.

27 Claims, 19 Drawing Sheets

(56) References Cited

U.S. PATENT DOCUMENTS

| | | | | |
|---|---|---|---|---|
| 7,153,324 | B2 | 12/2006 | Case et al. | |
| 8,038,708 | B2 | 10/2011 | Case et al. | |
| 2003/0149477 | A1 | 8/2003 | Gabbay | |
| 2008/0183280 | A1 | 7/2008 | Agnew et al. | |
| 2010/0082094 | A1 | 4/2010 | Quadri et al. | |
| 2010/0114307 | A1 | 5/2010 | Agnew et al. | |
| 2010/0234939 | A1 | 9/2010 | Jaffe | |
| 2011/0301700 | A1* | 12/2011 | Fish | A61F 2/2418 156/60 |
| 2012/0130471 | A1 | 5/2012 | Shoemaker et al. | |
| 2017/0196685 | A1* | 7/2017 | Yoshida | A61L 27/367 |
| 2018/0185143 | A1* | 7/2018 | Fish | A61F 2/2415 |
| 2021/0228347 | A1 | 7/2021 | Fish et al. | |

FOREIGN PATENT DOCUMENTS

| | | | |
|---|---|---|---|
| EP | 1659992 | B1 | 3/2013 |
| WO | 2022040120 | A1 | 2/2022 |

OTHER PUBLICATIONS

International Application No. PCT/US2023/021857, International Filing Date May 11, 2023, International Search Report, dated Jun. 30, 2023.

International Application No. PCT/US2023/021868, International Filing Date May 11, 2023, International Search Report, dated Aug. 3, 2023.

International Application No. PCT/US2023/021873, International Filing Date May 11, 2023, International Search Report, dated Aug. 10, 2023.

* cited by examiner

TRANSCATHETER VALVE SYSTEM AND METHOD FOR VENOUS INSUFFICIENCY FIGURES
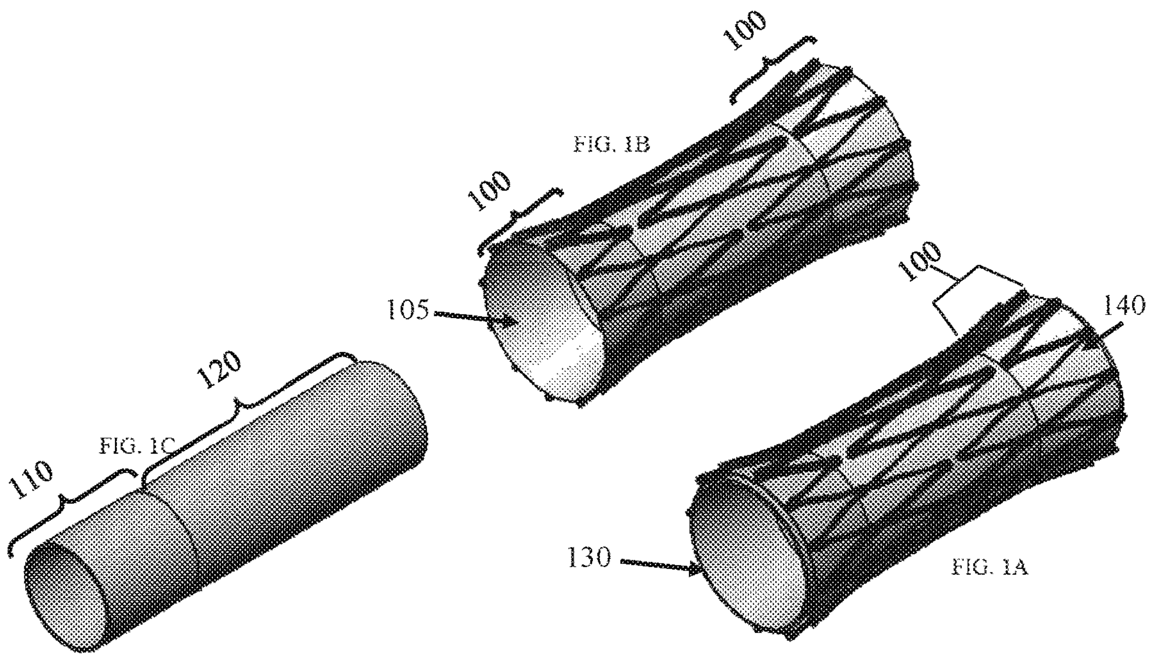
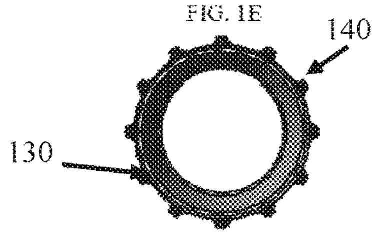
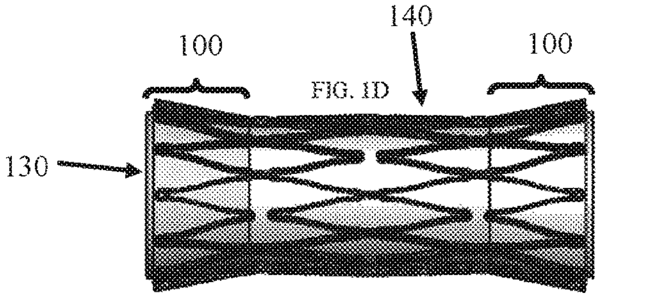

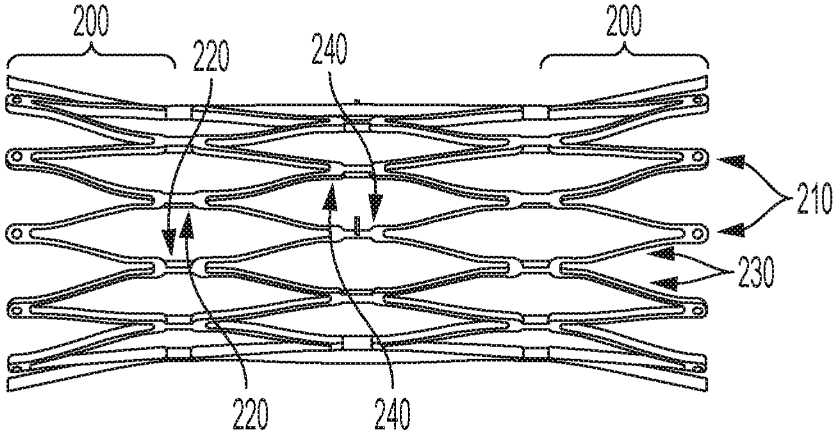
FIG. 2
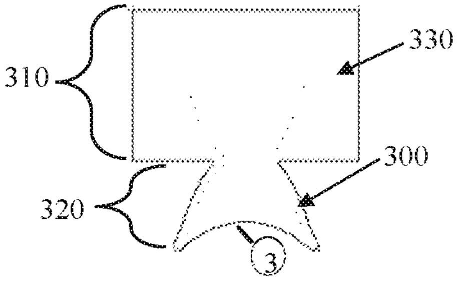
FIG. 3A
FIG. 3B
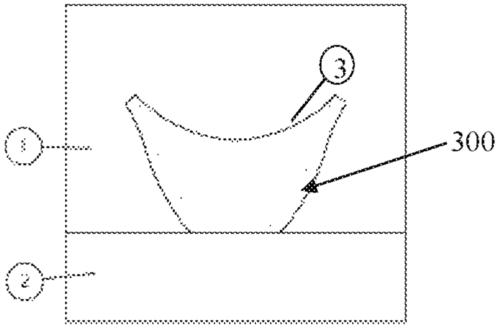
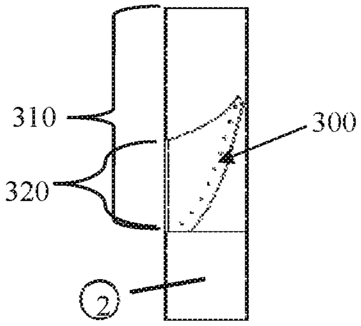
FIG. 3C

| Parameter | Units | Potential Range | Actual Range |
|---|---|---|---|
| Coaptation Angle, α | Deg | 20 – 80 | 30 – 65 |
| β (free margin angle between commissure points) | Deg | 90 – 270 | 110 – 130 |
| Leaflet Total Height, A+B | mm | 6 – 11 | 7 – 10 |
| A+B to Coaptation Height Ratio | N/a | 0.5 – 1.0 | 0.85 – 0.95 |
| Commissure-to-Commissure (CC), Flat Width | mm | 12 – 20 | 16 – 18 |
| Coaptation Gap, b | mm | 0 – 3 | 0 – 2 |
| S (free margin distance) | mm | 14 – 27 | 17 – 22 |

TRANSCATHETER VALVE SYSTEM AND METHOD FOR VENOUS INSUFFICIENCY

CROSS-REFERENCE TO RELATED APPLICATIONS

This application is a continuation of U.S. application Ser. No. 18/196,121 filed May 11, 2023, which claims priority to and the benefit of Provisional Application No. 63/340,867, filed on May 11, 2022 and Provisional Application No. 63/404,150, filed on Sep. 6, 2022, the contents of which are hereby incorporated by reference in their entireties.

FIELD

The present invention generally pertains to a transcatheter anti-reflux venous valve endoprosthesis system, its methods of manufacture and its uses.

BACKGROUND OF THE INVENTION

Chronic venous insufficiency (CVI) describes a condition that affects the venous system of the lower extremities with venous hypertension causing various pathologies including pain, swelling, edema, skin changes, and ulcerations. It is characterized by failure of venous valves to allow blood from the lower limbs to return to the heart, resulting in venous hypertension. Incompetence in venous valves creates reflux, which can lead to pain, itching, and severe and uncontrollable swelling that can reduce mobility and result in severe prolonged ulcerations.

More serious consequences of CVI can include venous ulcers, which have an estimated prevalence of about 0.3%, although active or healed ulcers are seen in about 1% of the adult population. See Eberhardt RT, Raffetto JD. Chronic venous insufficiency. Circulation. (2005) May 10; 111(18): 2398-409. It has been estimated that about 2.5 million people have severe cases of CVI in the United States, and of those, about 20% develop venous ulcers. The overall prognosis of venous ulcers is poor, with delayed healing and recurrent ulceration being common. More than 50% of venous ulcers require prolonged therapy lasting more than a year. Individuals with CVI not only suffer the physical effects of the disease, but also endure psychological ailments caused by undesired color changes and bulging of the skin. In severe cases of CVI involving deep vein thrombosis and pulmonary embolism, death can occur.

The socioeconomic impact of venous ulceration also can be dramatic, resulting in an impaired ability to engage in social and occupational activities, thus reducing the quality of life and imposing financial constraints. Disability related to venous ulcers often leads to loss of productive work hours, estimated at 2 million workdays/year, and may cause early retirement, which is found in up to 12.5% of workers with venous ulcers DaSilva A, Navarro MF, Batalheiro J. "The importance of chronic venous insufficiency: various preliminary data on its medico-social consequences." Phlebologie. 1992; 45:439-43. The financial burden of venous ulcer disease on the healthcare system is readily apparent: an estimated $1 billion is spent annually on the treatment of chronic wounds in the United States, or up to 2% of the total healthcare budget in all Western countries, and recent estimates place the cost of venous ulcer care at $3 billion annually. See Eberhardt supra.

Currently, the approved therapies for treatment of CVI are limited mainly to compression garments, compression pumps, and wound dressings. See Raffetto JD. Dermal pathology, cellular biology, and inflammation in chronic venous disease. Thromb Res. (2009); 123 Suppl 4:S66-71.

In response to the need for improved treatments of patients suffering from CVI, enVVeno Medical Corporation of Irvine, California developed the VenoValve® system which offers a permanent, single-use implant for chronic venous insufficiency. The functional component of VenoValve® is a porcine aortic leaflet. VenoValve® is surgically implanted in the deep vein of the lower extremity by a licensed healthcare professional and sutured to the repaired vein. A description of the VenoValve® replacement valve is provided in U.S. Pat. No. 11,285,243 which is hereby incorporated by reference in its entirety.

A few other transcatheter valves have been disclosed which require use of multiple leaflets or stent or frame design to differentiate between inflow and outflow of blood when placed in the veins.

For example, Published U.S. Application No. 20170196692, which is hereby incorporated by reference in its entirety, describes an implantable valve having a bulbous center section. The valve can supposedly be implanted using a transcatheter delivery system, but the system requires a capability to engage and release a valve with an enlarged bulbous section, which is wider than natural human vein.

Published U.S. Application No. 20190328511, which is hereby incorporated by reference in its entirety, discloses a prosthetic transcatheter valve device with a distinct an anterograde end and a retrograde end. The anterograde end of the device comprises a pair of leaflets opposingly positioned with respect to one another.

Published U.S. Application 20090254175, which is hereby incorporated by reference in its entirety, discloses a meshed stent with lattices, where both its ends have spiral struts. The stent can house at least two leaflets to create a one-way flow valve.

U.S. Pat. No. 7,744,642, which is hereby incorporated by reference in its entirety, describes a prosthetic transcatheter valve with a hollow base disposed as an inflow end, a plurality of struts connected with that base and extending to a blood outflow end; and inwardly oriented flanges disposed at the blood outflow ends of the struts. The valve has leaflets in gaps between the struts and are supported by the frame.

Published U.S. Application 20180078372, which is hereby incorporated by reference in its entirety, discloses a radially expandable frame with a plurality of leaflets frame has a distinct inflow and outflow end. The frame specifically requires a scalloped inflow and outflow edge as a functional feature.

Published U.S. Application No. 20030055492A1, which is hereby incorporated by reference in its entirety, also discloses a self-expandable prosthetic transcatheter valve comprising more than two leaflets and a wire frame with at least one zigzag section of the wire.

It has been observed that the ability to accurately guide and position the transcatheter valve for placement in a patient's deep venous system is affected by factors such as the valve shape, valve size, target position, for example, where the device is to be moved through or positioned across venous walls and/or at tortuous anatomy. There may also be issues with the coupling between the vein frame used for the valve to be delivered, all of which can result in a less accurate, and therefore less safe, device delivery process.

Given the prevalence and socioeconomic impact of CVI, an additional, alternative and effective treatment for CVI which is less surgically invasive than current approaches and employs a monocusp valve is desirable, particularly for patients who are candidates for the transcatheter system described herein.

SUMMARY

The present invention provides a novel system design and delivery for the treatment of chronic venous insufficiency.

A transcatheter valve system for implantation into a host vein of a subject is described. The transcatheter valve system can comprise a valve assembly.

In accordance with an exemplary embodiment, the valve assembly can comprise at least one leaflet formed using a continuous biological tissue.

In one aspect of the embodiment, the at least one leaflet can be formed from a flat sheet of the continuous biological tissue that is folded form a monocusp shape. In an exemplary embodiment, the exact geometry is not being replicated, but the function of the native valve is achieved by opening and closing under physiologically relevant pressure gradients causing the vortex operation with respect to blood flow using a monocusp leaflet that allows the leaflet to open and to smoothly and quickly close. The at least one leaflet's cusp can be folded from a continuous biological tissue, and thus suturing is not required to form the apex of the leaflet's cusp. However, suturing can be used to form the margins of the leaflet's cusp.

In an exemplary aspect, the biological tissue can be from a xenogeneic source.

In one aspect, the xenogeneic source is selected from the group consisting of porcine, bovine, and equine. In a preferred aspect, the xenogeneic source is porcine. In another aspect, the xenogeneic source is xenogeneic pericardium. In another aspect, the xenogeneic source is porcine pericardium.

In one aspect, the valve assembly can comprise exactly one leaflet. In one aspect of the exemplary embodiment, the leaflet's cusp is further formed by cutting the continuous biological tissue to a shape having a top section resembling the shape of a cusp and a bottom section (wall) that is generally rectangular in shape; folding the top section over the bottom rectangular section such that the apex of the leaflet's monocusp is created; and suturing the top section onto the bottom rectangular section of the biological tissue to form margins of the monocusp. In one aspect, an inflow skirt (inflow conduit) is attached to the wall (e.g., the rectangular shaped bottom section), which provides a way to avoid flow disruption on the inflow side of the device.

In a further aspect, the inflow skirt is attached to the wall and leaflet. In some specific aspects, the inflow skirt material can be made using a biological tissue from a xenogeneic source. The xenogeneic source can be selected from the group consisting of porcine, bovine, and equine. In one aspect, the xenogeneic source is porcine. In another aspect, the xenogeneic source is pericardium. In another aspect, the xenogeneic source is a porcine pericardium. In one aspect, the inflow skirt material has the same source as the monocusp leaflet. In yet another aspect, the inflow skirt material has a shape that is approximately rectangular. In a further aspect, the inflow skirt material has a generally square shape.

In more specific aspects, the biological tissue is fixed/crosslinked for certain period of time in a fixative. In a further aspect, the fixative is a solution that includes glutaraldehyde, formaldehyde, osmium tetroxide, genipin, hexamethylene diisocyanate (HMDI), a chemical or a naturally occurring fixative. In one aspect, the fixative is glutaraldehyde. In another aspect the fixative is 0.2% buffered isotonic glutaraldehyde.

In some aspects, the biological tissue is treated with a solution to reduce bioburden levels post fixation. In more specific aspects, the bioburden reduction solution is a mixture of Isopropyl Alcohol (IPA) and buffered isotonic glutaraldehyde. In a specific aspect, the bioburden reduction solution has about 1% to 80% IPA included in the solution mixture. In one aspect, the bioburden reduction solution has about 20% IPA included in the solution mixture.

In some other aspects, the biological tissue and the inflow skirt are attached to another skirt, which is located on the circumference. In some specific aspects, the skirt material can be made using a fabric skirt. Such fabric can include PET, PTFE fabric, ePTFE, degradable scaffold, collagen scaffold, hyaluronic acid scaffold, fibrin, a polymer based degradable or non-degradable material, or a biologic material. In one specific embodiment, the material has ultra-low profile, adequate porosity and suture retention, surface roughness, scaffold for cell attachment, and surface area able to attract migrated native cells to promote tissue ingrowth for improved device sealing and long-term device migration resistance post-implantation.

In yet another aspect, the skirt material has a shape that is approximately rectangular. In a further aspect, the skirt material has a generally rectangular shape with slightly wider sections (flared) at inflow and/or outflow. In some specific aspects, the skirt material has a shape that matches the shape of the wall and inflow skirt when attached together.

In one aspect, the at least one leaflet is attached to a frame. In another aspect, the at least one leaflet is attached to the frame using sutures. The at least one leaflet can be attached to the frame such that it partially covers the circumference of the frame. In another aspect, the at least one leaflet is attached to the frame such that it fully covers the circumference of the frame.

In one exemplary aspect, the at least one leaflet attached to an inflow skirt material is attached to a frame. In one aspect, the at least one leaflet attached with the inflow skirt material is attached to the frame using sutures.

In one exemplary embodiment, the sutures are a polybutester monofilament suture used to attach the inflow skirt material, the wall, and leaflet to the frame. In one aspect, the at least one leaflet attached with the inflow skirt material is attached to the frame, wherein the at least one leaflet attached with the inflow skirt material is attached to the frame partially covers the circumference of the frame. In another aspect, the at least one leaflet attached with the inflow skirt material is attached to the frame, wherein the at least one leaflet attached with the inflow skirt material is attached to the frame fully covers the circumference of the frame. In another aspect, the at least one leaflet attached with the inflow skirt material is attached to the frame using sutures.

In any of these exemplary aspects, the leaflet may be covered with a fabric skirt before suturing it into a frame. Also, in any of these exemplary aspects, the at least one leaflet attached to an inflow skirt material may be covered with a fabric skirt before suturing it to a frame.

In one exemplary embodiment, the at least one leaflet attached with the inflow skirt material when folded into a cylinder and attached to the circumferential fabric skirt attached to the frame, has an outer diameter of about 6 to about 18 mm. In one aspect, the at least one leaflet attached with the skirt material when folded into a cylinder and attached to the circumferential fabric skirt attached to the frame, has an outer diameter of about 9 mm to about 12 mm. The circumferential fabric skirt material helps prevent migration and aids in sealing that prevents flow circulation around valve.

In accordance with yet another exemplary embodiment, a method of manufacturing a replacement transcatheter valve for a subject is described. The method comprises providing a continuous biological tissue subjected to a fixation treatment; cutting the fixated biological tissue in a specific shape to have a top section and a bottom section; folding the top section onto the bottom such that an apex of a monocusp of a leaflet is created; and suturing the top folded section onto the bottom folded section along the margins to form the monocusp shape of the leaflet. The method can further comprise attaching the monocusp leaflet onto a tissue (inflow) skirt with sutures. The method can further comprise attaching the monocusp leaflet sutured to the tissue inflow skirt onto a fabric skirt.

In one aspect of the embodiment, the top section can resemble a shape of a native cusp. In another aspect, the bottom section is approximately rectangular in shape.

In one aspect, the specific shape of the cut biological tissue is as represented in FIG. 3A.

In one aspect, the continuous biological tissue can be from a xenogeneic source.

In another aspect, the xenogeneic source is selected from the group consisting of porcine, bovine, and equine. In one aspect, the xenogeneic source is porcine. In another aspect, the xenogeneic source is pericardium. In yet another aspect, the xenogeneic source is porcine pericardium.

In an exemplary embodiment, the exact geometry is not being replicated, but the function of the native valve is achieved by opening and closing under physiologically relevant pressure gradients causing the vortex operation with respect to blood flow using a monocusp leaflet that allows the leaflet to open and to smoothly and quickly close. The at least one leaflet's cusp can be folded from a continuous biological tissue, and thus suturing is not required to form the apex of the leaflet's cusp. However, suturing can be used to form the margins of the leaflet's cusp. In one aspect, the monocusp shape replicates the spherical geometry of a native valve with an apex and margins to provide a spatial buffer between the monocusp and the valve wall when the valve is in the open position, preventing or reducing adherence of the monocusp to the valve wall and facilitating closing of the monocusp valve when adequate flow pressure gradient is created.

In a further aspect, inflow skirt material can be attached to the wall and made using a biological tissue from a xenogeneic source. The xenogeneic source can be selected from the group consisting of porcine, bovine, and equine. In one aspect, the xenogeneic source is porcine. In another aspect, the xenogeneic source is a pericardium. In another aspect, the xenogeneic source is a porcine pericardium. In yet another aspect, the inflow skirt material has the same source as the monocusp leaflet.

In one exemplary embodiment, the method of manufacturing comprises attaching the leaflet to a frame. In one aspect, the method comprises attaching the leaflet to the frame using sutures. In another aspect, the method comprises attaching the leaflet to the frame such that it partially covers the circumference of the frame. In another aspect, the method comprises attaching the leaflet to the frame such that it fully covers the circumference of the frame.

In one exemplary embodiment, the method of manufacturing comprises attaching the leaflet attached to the inflow skirt material to a frame. In one aspect, the method comprises attaching the leaflet attached to the inflow skirt material to the frame using sutures. In another aspect, the method comprises attaching the leaflet attached to the inflow skirt material to the frame such that it partially covers the circumference of the frame. In another aspect, the method comprises attaching the leaflet attached to the inflow skirt material to the frame such that it fully covers the circumference of the frame.

In any of these aspects, the method of manufacturing can comprise attaching the leaflet to a fabric skirt before suturing it to a frame. Also in any of these aspects, the method of manufacturing can comprise attaching the leaflet attached to an inflow skirt material to a fabric skirt before suturing it to a frame. In one aspect, the fabric skirt can be natural or synthetic. In another aspect, the fabric is polyethylene terephthalate (PET). In yet another aspect, the fabric is such that the material has ultra-low profile, adequate porosity and suture retention, surface roughness, scaffold for cell attachment, and surface area able to attract migrated native cells to promote tissue ingrowth for improved device sealing and long-term device migration resistance post-implantation.

In accordance with an exemplary embodiment, the valve assembly can comprise an implantable vein frame. The design of the vein frame described herein addresses deployment issues in part due to the frame being compressible and expandable such as self-expanding with cellular geometry, structures and holes for holding sutures, as well as strut members, cells, and crowns (with or without anchors) employed on the surface of the frame.

In one exemplary embodiment, the implantable frame has anchors or hooks at the distal end of the flared cylinder to help prevent migration upon implantation. In some aspects, the anchors or hooks help aid the attachment of the vein frame, before the PET skirt has encouraged cell and tissue growth into the device. In some aspects, the anchors or hooks prevent traveling of the frame soon after insertion. In another aspect, the anchors or hooks may be located along the cylinder and are capable of grasping and/or anchoring into the native vein. The anchor or hooks may also be located at certain sections along the cylinder, such as the medial sections. The anchors or hooks along the cylinder may also take the form of individual tines. The anchors or hooks may be configured with different sizes based on the native vein.

In one exemplary embodiment, the implantable frame can comprise a first section, a second section, a third section, and a fourth section such that each section is interconnected to at least one other section. In some aspects, the first section is interconnected to the second section, the second section is interconnected to the third section and the first section, the third section is interconnected to the second section and the fourth section, and the fourth section is interconnected to the third section. In some aspects, the sections are interconnected with a strut member.

In some exemplary embodiment, each section can comprise about two to sixteen zigzag segments with two to sixteen proximal peaks and about two to sixteen distal peaks. In a preferred aspect, each section can comprise about twelve zigzag segments with about twelve proximal peaks and about twelve distal peaks. The design of the frame provides radial strength and is compressible. In some aspects, the sections are interconnected by connecting every alternating proximal peak of one section with alternating distal peak of the other section. In such aspects, there can be about six strut members between two sections. In some other aspects, the sections can be interconnected by connecting every third alternating proximal peak of one section with every third alternating distal peak of the other section. In such aspects, there can be about four strut members between two sections. In yet other aspects, the sections can be interconnected by every fourth alternating proximal peak of one section with every fourth alternating distal peak of the other section. In such aspects, there can be three strut members between two sections. In one aspect, the sections are rigidly interconnected using the strut members, which increases stability during valve placement while balancing enough flexibility during valve function and rigidity in the vein.

In some aspects, the implantable frame can have suture holes on one or both ends that can aid to attach the implantable frame to a valve assembly. In some specific aspects, the implantable frame has suture holes on both ends of the frame. In another embodiment, the suture holes are at the crowns of the frame zigzags. In another specific aspect, the suture holes have a diameter of about 0.5 mm, which allows frame durability and stress distribution optimization. In some aspects, the suturing holes can be about 0.3 mm to about 1.0 mm in diameter. The sutures can be stitched around each strut of the frame about three times. In another aspect, the sutures are stitched around each strut of the frame from about one to about five times. In another embodiment, the suture holes are at the crowns of the frame zigzags, where the crown can also be configured with anchors to reduce the potential for migration. In another aspect, anchors or hooks may be located along the cylinder and are capable of grasping and/or anchoring into the native vein. The anchor or hooks may also be located at certain sections along the cylinder, such as the medial sections. The anchors or hooks along the cylinder may also take the form of individual tines. The anchors or hooks may be configured with different sizes based on the native vein.

In some aspects, the implantable frame has flared ends. For example, one end of the implantable frame can have an outer diameter of D1 and the other end can have an outer diameter of D2. In some aspects, D1 and D2 are substantially different. In some other specific aspects, D1 and D2 are substantially similar. In some specific aspects, D1 and D2 can range from about 6 mm to about 18 mm, about 10.8 mm to about 14.4 mm.

In some aspects, the diameter of the implantable frame between the first section and the second section can have a diameter of D3. In some specific aspects, D3 can range from about 6 mm to about 18 mm, about 9 mm to about 12 mm. In some other aspects, D1 can be about 1 mm to about 3 mm larger than D3. A benefit of the size of the frame variations is to cater to different size veins and patient needs and to provide proper vein anchorage and to reduce the potential for migration.

In some aspects, the diameter of the implantable frame between the second section and the third section can have a diameter of D4. In some specific aspects, D4 can range from about 6 mm to about 18 mm, about 9 mm to about 12 mm. In some other specific aspects, D1 can be about 1 to about 3 mm larger than D4.

In some aspects, the diameter of the implantable frame between the third section and the fourth section can have a diameter of D5. In some specific aspects, D5 can range from about 6 mm to about 18 mm, about 9 mm to about 12 mm. In some other specific aspects, D1 can be about 1 to about 3 mm larger than D5. In some specific aspects, D3 and D5 are substantially different. In some other specific aspects, D3 and D5 are substantially similar.

In one exemplary embodiment, the implantable frame can be flared at one end of the frame. In some aspects, the outer diameter of the flared end can be less than about 18 mm. In preferred aspects, the outer diameter of the flared end can be about 10.8 mm to about 14.4 mm.

In another exemplary embodiment, the implantable frame can be flared at both ends of the frame. In some aspects, the outer diameter of the flared ends can be less than about 18 mm. In preferred aspects, the outer diameter of the flared ends can be about 10.8 mm to about 14.4 mm.

In some aspects, the zigzag segments in the implantable frame creates cells. In some aspects, the number of cells in the implantable frame is less than or equal to about 32. In some aspects, the number of cells in the implantable frame is about 24. In some aspects, the number of cells present in the implantable frame provide sufficient radial strength of about 2-60 N, and to a range of about 17-20 N.

In some aspects, the size of the strut members between two specific sections can be different. For example, the size of strut members between the first section and the second section and the size of strut members between the third section and the second section can be different.

In some aspects, the size of the strut members between two specific sections can be significantly similar. For example, the size of strut members between the first section and the second section and the size of strut members between the third section and the second section can be the same.

In one exemplary embodiment, the implantable frame is self-expanding once crimped. In one embodiment, the frame is crimpable with a radial strength of about 17-20 N. In some aspects, the implantable frame comprises a material capable of significant recoverable strain to assume a low profile for delivery or implantation. After release of the compressed self-expanding frame, it is preferred that the implantable frame be capable of radially expanding back to its original diameter or close to its original diameter. In some aspects, the implantable frame is made from material with high elastic strain (such as super elastic) to undergo large deformations and immediately return to its undeformed shape, and is heat treated.

Particularly preferred materials for self-expanding implantable frames include shape memory alloys that exhibit superelastic behavior (e.g., are capable of significant distortion without plastic deformation). Frames manufactured of such materials may be significantly compressed without permanent plastic deformation, for example so that that can be compressed such that the maximum strain level in the stent or frame is below the recoverable strain limit of the material. Discussions relating to nickel titanium alloys and other alloys that exhibit behaviors suitable for frames can be found in, for example, U.S. Pat. No. 5,597,378 (Jervis), which is hereby incorporated by reference in its entirety, and International Application WO 95/31945 (Burmeister et al.), which is hereby incorporated by reference in its entirety. A preferred shape memory alloy is Ni—Ti, although any of the other known shape memory alloys may be used as well. Such other alloys include: Au—Cd, Cu—Zn, In—Ti, Cu—Zn—Al, Ti Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. One suitable material possessing desirable characteristics for self-expansion is Nitinol, a Nickel-Titanium alloy that can recover elastic deformations of up to 10 percent. This unusually large elastic range is commonly known as superelasticity.

In one exemplary embodiment, the implantable frame is capable of being expanded by use of a balloon. Such a frame may not be self-expanding. In some aspects, the implantable frame may be manufactured from an inert, biocompatible material with high corrosion resistance that can be plastically deformed at low moderate stress levels, such as tantalum. The implantable frames can be deployed by both assisted (mechanical) expansion (e.g., balloon expansion, and self-expansion means). In some aspects, the implantable frame can be made from materials that can be plastically deformed through the expansion of a mechanical assist device. When the balloon is deflated, the implantable frame can remain substantially in the expanded shape. Other acceptable materials include stainless steel, cobalt chromium, titanium ASTM F63-83 Grade 1, niobium or high carat gold K 19-22. One widely used material for balloon expandable structures is stainless steel, particularly 316 L stainless steel. Alternative materials for mechanically expandable structural frames that maintain similar characteristics to stainless steel include tantalum, platinum alloys, niobium alloys, and cobalt alloys.

In one exemplary embodiment, an implantable frame can also be coated with or formed from one or more degradable synthetic materials (e.g., polymers) and/or naturally derived materials (e.g., biological materials), as well as copolymers of degradable polymers and/or biological materials. A bioactive material can be mixed with or copolymerized with the bioabsorbable polymer or biological material. Alternatively, the bioactive material or a mixture of bioactive material and biostable or bioabsorbable polymer or biological material can be coated with a second layer comprising a bioabsorbable polymer or biological materials.

Bioabsorbable polymers or biological materials can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers, collagen, chitosan, hyaluronic acid, and fibrin. In one aspect, the implantable frame can be coated with a coating of between about 1 μm and about 50 μm, or between about 3 m and about 30 μm, although any suitable thickness can be selected.

In some aspects, upon implantation, absorption of the bioabsorbable polymer or biological materials can release a bioactive. Bioabsorbable polymers or biological materials can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers, collagen, chitosan, hyaluronic acid, and fibrin. In some aspects, the implantable frame can be coated with a coating of between about 1 m and about 50 μm, or between about 3 m and about m, although any suitable thickness can be selected. The coating can comprise a bioactive material layer contacting a separate layer comprising a carrier, a bioactive material mixed with one or more carriers, or any combination thereof. The carrier can be biologically or chemically passive or active but is selected and configured to provide a desired rate of release of the bioactive material. In some aspects, upon implantation, absorption of the bioabsorbable polymer or biological material does not release a bioactive. In some aspects, the implantable frame can tissue engineered (bio-engineered).

In another exemplary embodiment, the implantable frame is made of non-degradable materials. Some examples of non-degradable materials include polymers, metals, and biological materials. Such materials for implantable frame include those materials that can provide the desired functional characteristics with respect to mechanical load bearing, biological compatibility, modulus of elasticity, radio-opacity, or other desired properties. For some exemplary embodiments, the materials used to form the implantable frames can comprise a material that exhibits excellent corrosion resistance.

In some aspects, the material can be selected to be sufficiently radiopaque and create minimal artifacts during magnetic resonance imaging techniques (MRI). In some aspects, the implantable frame can comprise a metal, a metal alloy, a synthetic material, a naturally derived material, or any suitable combination thereof, for example as frame with multiple layers. In some aspects, the implantable frame can comprise nitinol, titanium, cobalt chromium, or PEEK. In a preferred aspect, the implantable frame is made of nitinol.

In one exemplary embodiment, the implantable frame may receive surface modification such as, but not limited to, electropolishing, passivation, anti-thrombogenic coating, coating with proper cell receptor binding sites embedded on the surface or in a biological or polymeric coating, coating that promotes tissue ingrowth, or a combination thereof.

In one exemplary embodiment, the implantable frame can allow radial compression of the implantable frame (e.g., crimping) resulting in a low profile to be used with a catheter delivery system. In some aspects, the crimpability of the implantable frame is about 6 Fr to about 20 Fr. In a preferred aspect, the crimpability of the implantable frame is about 12 Fr to about 16 Fr.

In one exemplary embodiment, the implantable frame can be fabricated using any suitable method known in the art. In some aspects, the complete frame structure is cut from a solid tube or sheet of material, and thus the implantable frame would be considered a monolithic unit. Laser cutting, water-jet cutting and photochemical etching are all methods that can be employed to form the structural frame from sheet and tube stock. Still other methods for fabricating and/or shape setting the complete frame structure as previously disclosed would be understood by one of skill in the art. Techniques for forming implantable frames are discussed, for example, in Dougal et al., "Stent Design: Implications for Restenosis." Rev. Cardiovasc Med. 3 (suppl. 5), S16-S22 (2002), which is incorporated herein by reference in its entirety.

In some embodiments, connections between the sections and zigzag segments may be by welding or other suitable connecting means. Other connection means include the use of a binder, heat, or chemical bond, and/or attachment by mechanical means, such as pressing, welding or suturing. In some aspects, portions of the implantable frame may be attached by applying a bonding coating. In a preferred aspect, the implantable frame is made by laser-cutting from raw tubing material of Nitinol with following dimensions: less than about 18 mm outer diameter, such as about 4 mm outer diameter, with thickness of less than about 1 mm, such as about 0.52 mm wall thickness.

In one exemplary embodiment, an implantable frame can optionally be sterilized using any suitable technique known in the art, or equivalents thereto. For example, an implantable frame can be sterilized using gamma radiation, ethylene oxide, solution, or electron beam sterilization with preference on gamma radiation. In some embodiments, a sterilized implantable frame satisfies a minimum Sterility Assurance Level (SAL) of about $10^{-6}$.

In one exemplary embodiment, the implantable frame or portion thereof can optionally comprise material that permits identification of the position or orientation of the implantable frame within a body passage. In some aspects, portions of the implantable frame can include a radiopaque material that can be identified by X-rays. In some aspects, the implantable frame can also comprise materials that are useful with contrast dyes to identify the implantable frame within a body passage. Non-limiting examples of radiopaque materials include, but are not limited to, high-density metals such as platinum, iridium, gold, silver, tantalum or their alloys, or radiopaque polymeric compounds. Radiopaque materials are highly visible under fluoroscopic illumination and are visible even at minimal thickness. In some aspects, the radiopaque material can be gold, platinum, tungsten, or iridium, as well as mixtures and alloys thereof, in an eyelet structure attached to one or more bridging member.

According to the aspects of the exemplary embodiment for the implantable frame, it may be seen variations may exist. It is further contemplated that other configurations of the implantable frame may exist, including for example variations having a fifth section.

The transcatheter system can comprise one or more aspects of a transcatheter valve and the implantable frame described above.

In one exemplary embodiment, a method comprising providing a transcatheter valve system for implantation into a host vein of a subject suffering from chronic venous insufficiency is disclosed.

In one aspect of the embodiment, the leaflet is formed from a sheet of the continuous biological tissue that is folded into a monocusp shape. The monocusp shape may replicate the spherical geometry of a native valve with an apex and margins. In an exemplary embodiment, the exact geometry is not being replicated, but the function of the native valve is achieved by opening and closing under physiologically relevant pressure gradients causing the vortex operation with respect to blood flow using a monocusp leaflet that allows the leaflet to open and to smoothly and quickly close. The at least one leaflet's cusp can be folded from a continuous biological tissue, and thus suturing is not required to form the apex of the leaflet's cusp. However, suturing can be used to form the margins of the leaflet's cusp. In another specific aspect, the suture holes have a diameter of about 0.5 mm, which allows durability and stress distribution optimization. In one exemplary aspect, the suture holes are spaced about 1.5 mm apart. In other aspects, suture holes can be spaced about 0.5 mm to about 3 mm apart from one another.

In another aspect, the suturing spacing reduces leakage with overlap of sutures. In one aspect, the monocusp shape replicates the spherical geometry of a native valve with an apex and margins to provide a spatial buffer between the monocusp and the valve wall when the valve is in the open position, preventing or reducing adherence of the monocusp to the valve wall and facilitating closing of the monocusp valve when adequate flow pressure gradient is created. The leaflet's cusp does not require suturing to form the apex of the leaflet's cusp. However, suturing can be used to form the margins of the leaflet's cusp. In one aspect, the leaflet's cusp is further formed by cutting the continuous biological tissue to a shape with a top section resembling the shape of a cusp and bottom rectangular section; folding the top section over the bottom rectangular section such the apex of the leaflet's monocusp is created; and suturing the top section to the bottom rectangular section of the biological tissue to form margins of the monocusp.

In accordance with another exemplary embodiment, a transcatheter delivery device is provided. The present invention effectively provides a delivery system wherein the delivery device can be manipulated and guided to implant a transcatheter valve into a vein. The delivery device includes, for example, an inner tube assembly, a sheath assembly, a catheter assembly, and a handle.

The inner tube assembly can include a flush port and a hypotube.

The sheath assembly includes nose cone and a nose cone-braided shaft. In one aspect, the sheath assembly is connected to the inner tube assembly by having the hypotube of the inner tube assembly cover the nose cone-braided shaft of the sheath assembly partially or completely. The catheter assembly is configured to contain the transcatheter valve in a compressed arrangement. The catheter assembly can be slidably placed over the sheath assembly, and includes a proximal region and a distal region. In one aspect, one end of the proximal region of the catheter assembly is connected to the handle and the other end of the proximal region of the catheter assembly is connected to the distal region of the catheter assembly.

In another aspect, one end of the distal region of the catheter assembly is configured to compressively contain the transcatheter valve in a compressed arrangement and the other end of the distal region of the catheter assembly is connected to the proximal region of the catheter assembly. The distal region of the catheter assembly can be configured to compressively contain the transcatheter valve has two shapes. The first shape has a first diameter and the second shape has a second diameter. Both the shapes can be contiguous in nature or assembled.

The handle is configured to selectively move the catheter assembly relative to the sheath assembly. The delivery device can be configured to provide a resting state in which the distal region of the catheter assembly is closer to the nose cone and a delivery state in which the distal region of the catheter assembly is pulled away from the nose cone. The distal section of catheter is pulled back by turning the knob on the handle, causing the valve to be exposed; therefore, the handle causes the distal section of catheter to slide back over the nose cone sheath.

In one exemplary embodiment, the delivery device includes an indicator for when the self-expanding valve can no longer be repositioned. The indicator aids the placement and timing of delivery of the valve, as it is clear how far the valve extrudes from the delivery device. A further embodiment of the indicator can indicate when approximately 20% of valve deployment that the valve can no longer be retracted into the delivery device.

In a preferred exemplary embodiment, the delivery system provides three functions in one, as the device acts as a dilator, introducer sheath, and delivery system. In this embodiment, the three in one system allows for the device to not separately need a dilator or introducer sheath, as the tapered bullet shape nose cone provides atraumatic entry acting as a dilator and the distal region of catheter assembly has a continuous and uniform diameter acting as an introducer sheath.

The disclosure also provides an improved method of treating chronic venous insufficiency (CVI) over conventional methods which manage CVI by deactivation of incompetent veins through chemical or mechanical blockage. The transcatheter valve described herein prevents blood reflux without permanently deactivating the damaged veins, thus providing an improved method for treating CVI by replacing and restoring functions of incompetent valves to maintain proper blood flow.

The disclosure also provides a system for treating CVI in patients. The system includes a transcatheter device and the delivery device as described above. The transcatheter device includes an implantable frame and a transcatheter valve attached to the frame. Upon assembly of the system to a resting condition, the catheter assembly in the delivery device compressively contains the transcatheter device in the compressed arrangement over the sheath assembly. The system can be transitioned to a delivery state in which the distal region of the catheter assembly is pulled away from the nose cone such that it exposes the transcatheter device over the nose cone for release from the delivery device.

The disclosure also provides a method for treating chronic venous insufficiency in patients. The method includes receiving a transcatheter device including an implantable frame and a transcatheter valve attached to the frame. The delivery device includes an inner tube assembly, a sheath assembly, a catheter assembly, and a handle. The inner tube assembly includes a flush port and a hypotube. The sheath assembly includes nose cone and a nose cone-braided shaft. In one aspect, the sheath assembly is connected to the inner tube assembly by having the hypotube of the inner tube assembly cover the nose cone-braided shaft of the sheath assembly partially or completely. The catheter assembly is configured to contain the transcatheter valve in a compressed arrangement. The catheter assembly is slidably placed over the sheath assembly, and includes a proximal region and a distal region. In one aspect, one end of the proximal region of the catheter assembly is connected to the handle and the other end of the proximal region of the catheter assembly is connected to the distal region of the catheter assembly.

One end of the distal region of the catheter assembly can be configured to compressively contain the transcatheter valve in a compressed arrangement and the other end of the distal region of the catheter assembly is connected to the proximal region of the catheter assembly. In one aspect, the distal region of the catheter assembly configured to compressively contain the transcatheter valve can have two shapes. The first shape has a first diameter and the second shape has a second diameter. Both the shapes can be contiguous in nature or assembled. The handle is configured to selectively move the catheter assembly relative to the sheath assembly. The delivery device is configured to provide a resting state in which the distal region of the catheter assembly is closer to the nose cone and a delivery state in which the distal region of the catheter assembly is pulled away from the nose cone. In some aspects, the method comprises having the delivery device such that the catheter assembly in the delivery device compressively contains the transcatheter device in the compressed arrangement over the sheath assembly.

The transcatheter valve can comprise biological tissue from a xenogeneic source. The biological tissue can comprise at least one leaflet from a xenogeneic source such as porcine, bovine, and equine. In some aspects, the at least one leaflet of the transcatheter valve is attached to an inflow skirt material, as described above. The method further comprises providing a frame to which is attached through the fabric skirt of the transcatheter valve. The transcatheter valve can be attached to the frame such that it partially or fully covers the circumference of the frame. In a specific aspect, the at least one leaflet attached with the skirt material is attached to the frame using sutures.

In one aspect, the method further comprises creating a fenestration in the host vein, the fenestration having a shape generally corresponding to the patch. In the preceding aspect, the fenestration may be created generally on the external iliac vein, iliac vein, femoral vein, common femoral vein, popliteal vein, superficial vein system, great saphenous vein, *profunda* vein, or the external jugular vein. The method may further comprise attaching the transcatheter valve to the host vein at the fenestration. In a still further aspect, the transcatheter have been subjected to a fixation treatment. In any of these aspects, the subject may be human.

BRIEF DESCRIPTION OF THE DRAWINGS

FIG. 1A is a longitudinal view of a venous valve with a fabric skirt covered frame, inflow skirt, and leaflet according to an exemplary embodiment.

FIG. 1B is a longitudinal view of a venous valve fabric skirt covered frame according to an exemplary embodiment.

FIG. 1C is a longitudinal view of a venous valve leaflet attached to inflow tissue skirt according to an exemplary embodiment.

FIG. 1D is a side perspective of a venous valve with a fabric covered frame, inflow skirt, and leaflet according to an exemplary embodiment.

FIG. 1E is a front cross-sectional perspective of a venous valve with a fabric covered frame, inflow skirt, and leaflet according to an exemplary embodiment.

FIG. 2 is a side perspective of a venous valve frame according to an exemplary embodiment.

FIG. 3A is a 2-D flat view of a leaflet according to an exemplary embodiment.

FIG. 3B is a 2-D flat view of a wall with leaflet and inflow skirt, where the monocusp is folded onto the wall and the inflow skirt is attached to the base of the leaflet according to an exemplary embodiment.

FIG. 3C is a side perspective of a longitudinal view of a leaflet folded onto the wall and attached to an inflow skirt to form a conduit according to an exemplary embodiment.

FIG. 41 is complete tissue leaflet with the completed inflow skirt fully sutured to leaflet, where the leaflet and skirt folded and sutured on ends in the axial/longitudinal direction in anticipation for insertion and fixation in the frame in an exemplary embodiment.

DETAILED DESCRIPTION

Figures 3D, 3E:
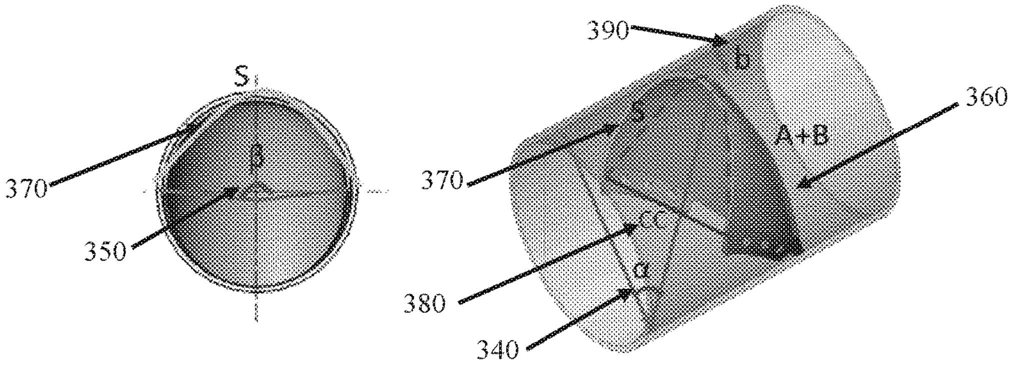
FIGS. 3D and 3E are an overview of parameters considered for a 10 mm transcatheter venous valve and a representative monocusp belly curve in an exemplary embodiment.

FIGS. 1A, 1D, and 1E show the fabric covered frame assembly, wherein the frame 140, leaflet 130 and FIG. 1C 120, wall FIG. 1C 120, and inflow skirt FIG. 1C 110 have been fixed together. FIG. 1A is a longitudinal view of the assembled transcatheter valve, where the leaflet 130 is complete with a supporting wall FIG. 1C 120 and attached inflow skirt FIG. 1C 110 in a fabric covered frame assembly. In FIG. 1A, the ends 100 of the frame are flared. The flared ends 100 can be between about 2 mm to about 10 mm from the beginning of the flare to the end of the flare. FIG. 1B is a longitudinal view of the fabric 105 covered frame assembly.

FIG. 1C is a longitudinal view of the assembled leaflet and inflow skirt prior to insertion to the covered frame in one embodiment. In FIG. 1C, the inflow skirt is identified as 110, where the continuous biologic leaflet is identified as 120. In 120 of FIG. 1C it shows one leaflet that has been formed from a flat sheet of the continuous biological tissue that is folded form a monocusp shape with a supporting wall. FIG. 1D is a side perspective of the assembled transcatheter valve, where the leaflet is complete with a supporting wall and attached inflow skirt in a covered frame assembly. FIG. 1E is a front perspective of the assembled transcatheter valve, where the leaflet is complete with a supporting wall and attached inflow skirt in a covered frame assembly.

FIG. 2 is a venous valve frame without the covering in an exemplary embodiment. FIG. 2 shows flared ends of the frame which are identified as 200. The eyelets in the crown of the frame are shown as 210 in FIG. 2. The bridges of the frame are shown at 220 in FIG. 2. The struts of the frame are shown as 230 in FIG. 2. In a preferred exemplary embodiment, each section can comprise about twelve zigzag segments with about twelve proximal peaks 240 and about twelve distal peaks 240. The design of the frame provides radial strength and is compressible. In some aspects, each section can comprise about four to sixteen proximal peaks and about four to sixteen distal peaks.

In some aspects, the sections are interconnected by connecting every alternating proximal peak of one section with alternating distal peak of the other section. In such aspects, there can be about six strut 230 members between two sections. In some other aspects, the sections can be interconnected by connecting every third alternating proximal peak of one section with every third alternating distal peak of the other section. In such aspects, there can be about four strut members between two sections. In one aspect, the sections are rigidly interconnected using the strut members, which increases stability during valve placement while balancing enough flexibility during valve function and rigidity in the vein. In one aspect, the geometry of interconnections formed by connecting every alternating proximal peak of one section with alternating distal peak of the other section provide enough flexibility to accommodate and mimic the natural dilation and contraction of a vein, ensuring optimal stress distribution, and providing a proper fit across a broad range of vein sizes. In one aspect, the geometry of the interconnections are designed with enough flexibility to accommodate and mimic the natural dilation and contraction caused by momentary increases in pressure and/or blood flow, including increases caused by activity of muscles such as the calf muscle (e.g., during calf muscle contraction) and/or Valsalva maneuver.

FIG. 2 is an implantable frame that has suture holes 210 on one or both ends that can aid to attach the implantable frame to a valve assembly. In some specific aspects, the implantable frame has suture holes on both ends of the frame. In another embodiment, the suture holes 210 are at the crowns 210 of the frame zigzags.

FIG. 3A is a cross-sectional view of an exemplary leaflet according to an exemplary embodiment of the present invention showing the leaflet without an inflow skirt attached.

In one aspect of the exemplary embodiment, the leaflet's cusp is further formed by cutting the continuous biological tissue to a shape having a top section 320 resembling the shape of a cusp and a bottom section 310 that is generally rectangular in shape; folding the top section 330 over the bottom rectangular section such that the apex of the leaflet's monocusp is created; and suturing the top section onto the bottom rectangular section of the biological tissue to form margins of the monocusp, which is FIG. 3B. The entire leaflet is FIG. 3A, where the top portion 320 is the cusp portion and 310 is the bottom portion, where 3 is the belly curve before folded. The outline of the where the top section 320 is folded is shown as 330.

FIG. 3B is a side perspective of the cross-sectional leaflet with supporting wall 1 and inflow skirt 2, where the inflow skirt 2 is attached to the base of the leaflet in an exemplary embodiment. In one aspect, an inflow skirt is attached to the wall, which provides a way to avoid flow disruption on the inflow side of the device. In a further aspect, the inflow skirt 2 is attached to the wall and leaflet 1. In some specific aspects, the skirt 2 material can be made using a biological tissue from a xenogeneic source. The xenogeneic source can be selected from the group consisting of porcine, bovine, and equine. In one aspect, the xenogeneic source is porcine. In another aspect, the xenogeneic source is a xenogeneic pericardium. In another aspect, the xenogeneic source is a porcine pericardium. In an aspect, the skirt 2 material has a shape that is approximately rectangular.

FIG. 3C shows a side perspective of a folded leaflet 310 with skirt 2 where suture holes 300 can be seen. The monocusp 320 is folded and the leaflet 310 with skirt 2 is folded. In one embodiment, the leaflet has multiple cusps, which could be bicuspid or tricuspid shape. In one embodiment, the design of the leaflet includes a belly curve, described further in connection with FIG. 3D.

FIG. 3D illustrates the various design shapes and angles in a leaflet for a transcatheter valve in accordance with an exemplary embodiment, including a preferred design that provides for beneficial operation of the valve and leaflet. For example, for a 10 mm transcatheter venous valve, it can have a coaptation angle 340 of about 20-80 degrees, a free margin angle 350 between commissure points of about 90-270 degrees, a leaflet total height 360 of about 6 mm-11 mm, an A+B to coaptation height ratio of about 0.5-1, a commissure-to-commissure (CC)/flat width 380 of about 12 mm-20 mm, a coaptation gap 390 of about 0-3 mm, and a free margin distance 370 of about 14 mm-27 mm, as shown in FIG. 3E.

FIG. 3E shows an alternative exemplary embodiment where the leaflet FIG. 3A is formed for a 10 mm transcatheter venous valve having a preferred design that provides for beneficial operation of the valve and leaflet according to an exemplary embodiment. For example, the leaflet design includes various structural relationships such as belly curve having a coaptation angle of about 30-65 degrees, a free margin angle between commissure points of about 110-130 degrees, a leaflet total height of about 7 mm-10 mm, an A+B coaptation height ratio of about 0.85-0.95, a commissure-to-commissure (CC)/flat width of 16-18 mm, a coaptation gap of 0-2 mm, and a free margin distance of 17-22 mm.

A method for assembling a leaflet according to an exemplary embodiment of the present invention is illustrated in FIGS. 4A to 4I which show various stages of the leaflet 405 being formed. Inflow skirt 425 is fixed to the leaflet 405 in FIGS. 4E, 4G, 4H, and 4I. The inflow skirt can be attached to the leaflet only on the in-flow side of the leaflet to prevent wind socking issues. The inflow skirt material helps prevent migration and aids flow. The leaflet and inflow skirt may cover the entire valve in an exemplary embodiment.

In one exemplary embodiment, the at least one leaflet attached with the inflow skirt material when folded into a cylinder, has a diameter of about 6 to 12 mm. In one aspect, the at least one leaflet attached with the inflow skirt material when folded into a cylinder has a diameter of about 9 mm to about 12 mm.

In accordance with another exemplary embodiment, the method comprises providing a continuous biological tissue subjected to a fixation treatment; cutting the fixated biological tissue in a specific shape to have a top section and a bottom section; folding the top section onto the bottom such that an apex of a monocusp of a leaflet is created; and suturing the top folded section onto the bottom folded section along the margins to form the monocusp shape of the leaflet. The method can further comprise attaching the monocusp leaflet onto a tissue inflow skirt with sutures. The method can further comprise attaching the monocusp leaflet sutured to the tissue inflow skirt onto a fabric skirt.

In one exemplary aspect, the suture holes onto the tissue are spaced about 1.5 mm apart. In other aspects, suture holes can be spaced about 0.5 mm to about 3 mm apart from one another. In another aspect, the suturing spacing reduces leakage with overlap of sutures.

Figure 4A:
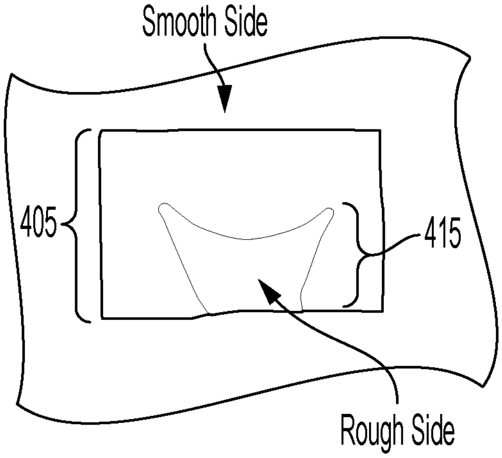
FIG. 4A is a folded over leaflet where the smooth side is mostly tissue elastin fibers and the rough side is mostly tissue collagen fibers where the tissue composition is about 80% collagen, and about 20% elastin in exemplary embodiment.

At the start of the leaflet manufacturing process, the at least one leaflet can be formed from a flat sheet of the continuous biological tissue that is folded form a monocusp shape. In an exemplary embodiment, the exact geometry is not being replicated, but the function of the native valve is achieved by causing the vortex operation with respect to blood flow using a monocusp leaflet that allows the leaflet to open and close quickly. The leaflet's cusp can be folded from a continuous biological tissue, and thus suturing is not required to form the apex of the leaflet's cusp. However, suturing can be used to form the margins of the leaflet's cusp. The leaflet in FIG. 4A is formed by laser cutting Porcine Pericardial Tissue into a rectangular shape, where the animal donors' cusp 415 remains intact.

Figure 4B:
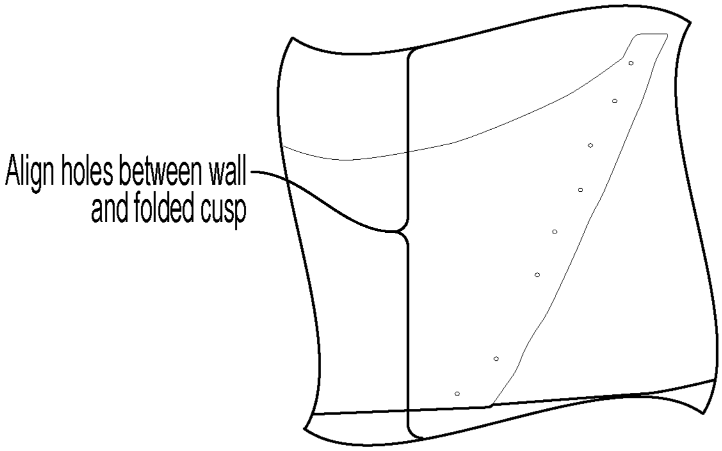
FIG. 4B is the alignment of the suture holes on the folded leaflet cusp to those suture holes on the supporting wall in an exemplary embodiment.
Figure 4C:
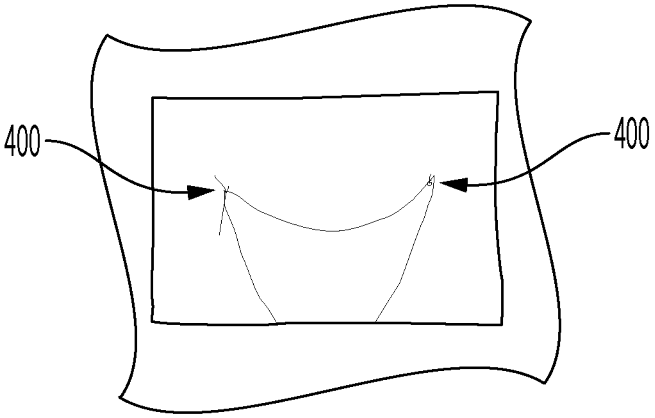
FIG. 4C is the fixation of temporary stitches on commissures of the folded leaflet in an exemplary embodiment.

In an exemplary embodiment, the smooth side of the leaflet, approximately a 10 mm, Porcine Pericardial Laser Cut Tissue, is formed. As shown in FIG. 4A, the smooth side can be elastin fiber and the rough side can be collagen, where the cross section is about 80% collagen, and about 20% elastin. As seen in FIG. 4A, the leaflet is folded over a supporting wall, which shown in FIG. 4B is sourced from a xenogeneic source, a porcine, in a laser cut rectangular shape with the smooth sides facing each other. The mono-cusp and the valve wall when the valve is in the open position, prevent or reduce adherence of the monocusp to the valve wall and facilitating closing of the monocusp valve when flow pressure is reduced.

In FIG. 4B, suture holes formed in the supporting wall are aligned with the folded leaflet cusp to those on the leaflet. Next, a sewing needle can be taken with temporary sutures like PTFE and woven through the first matching holes at the upper left side to secure it in place. The placed temporary sutures can be seen in FIG. 4C at 400. The sutures should be inserted into the suture holes and not into tissue surrounding the suture holes. Excess sutures can be removed. These steps can be repeated in order to secure the wall and leaflet to each other while more permanent sutures are being placed. The temporary sutures 400 reduce migration of the wall and leaflet and ensure the suture holes line up with the two pieces.

Figure 4D:
FIG. 4D is a complete tissue leaflet sutured to supporting wall without an inflow skirt and supporting wall suturing, after the two temporary sutures at the corners have been removed in an exemplary embodiment.

After the temporary sutures are in place, a sewing needle with polybutester, monofilament, non-absorbable surgical suture can be inserted into the first matching holes of the upper left side of the leaflet and supporting wall. FIG. 4D shows a complete tissue leaflet without a skirt and supporting wall suturing, after the two temporary sutures at the corners and the stitch of the cusp are completed. By inserting the suture and needle into the same matching hole with the temporary knot, the running stitch 410 can secure the wall to the leaflet. Excess sutures can be removed. In the next matching holes on the same side of the leaflet, sewing can be continued to make a double lock stitch. Once the last matching suture hole is reached, the needle can be passed through to make a triple lock-stitch. This process can be repeated to stitch the other side 410 of the leaflet cusp. FIG. 4D shows two temporary stitches at the corners of the leaflet commissures that can be removed using a suturing needle.

Afterwards, skirt 425 can be aligned to the inflow side of the leaflet 405. The skirt and leaflet can be oriented such that the smooth side of the skirt 425 and supporting wall FIG. 4B are visible. Skirt 425 can be folded on top of the leaflet 405 such that the rough side of the skirt is visible. The bottom edge of the skirt 420 can be aligned with the bottom edge of the leaflet and supporting wall. The side edges of the skirt should also be aligned with the side edges of the supporting wall. For assembly of the leaflet assembly, a sewing needle with a temporary suture like, PTFE, can be used. In an exemplary embodiment, the needle is inserted through the skirt 425 and out through the leaflet supporting wall and secure it, as shown in FIG. 4D at 410. The needle can be inserted approximately 1 mm from the lower edge of the tissue and 0.5 mm from the left edge of the tissue.

Figure 4E:
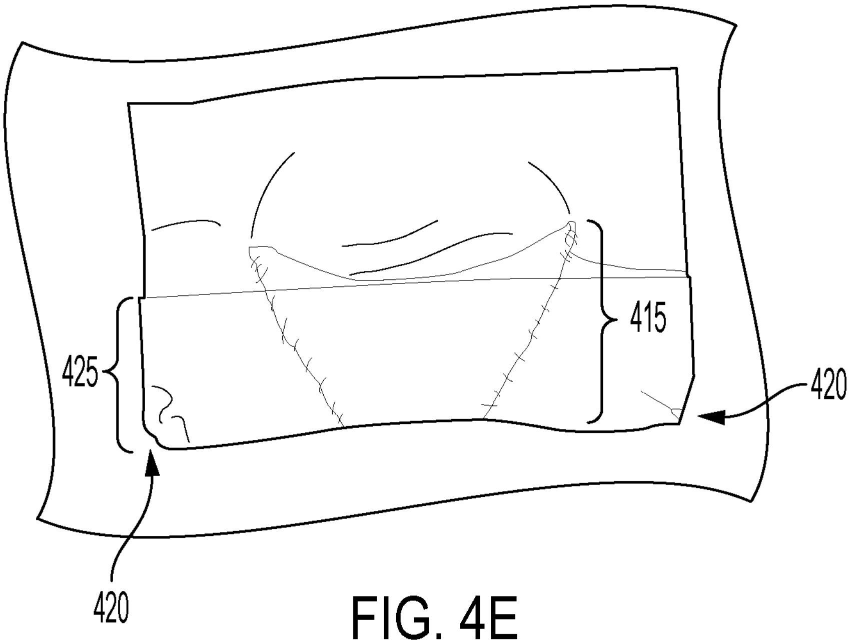
FIG. 4E is a complete tissue leaflet sutured to supporting wall with an inflow skirt and temporary stitches securing inflow skirt to the leaflet supporting wall in an exemplary embodiment.

FIG. 4E shows temporary sutures 420 on the right and left sides of leaflet and wall. Using, for example, a sewing needle with polybutester, monofilament, non-absorbable surgical suture and using the same suture hole as the temporary suture, the needle can be inserted through both the tissue skirt 425 and leaflet 405 to secure the skirt to the leaflet. The temporary suture can then be removed so that the leaflet's supporting wall can be sutured to the skirt 425 along the bottom edge using, for example, a double lock-stitch. Suturing can continue up to approximately 1 mm from the left side of the margin of attachment of the folded cusp 415.

Figure 4F:
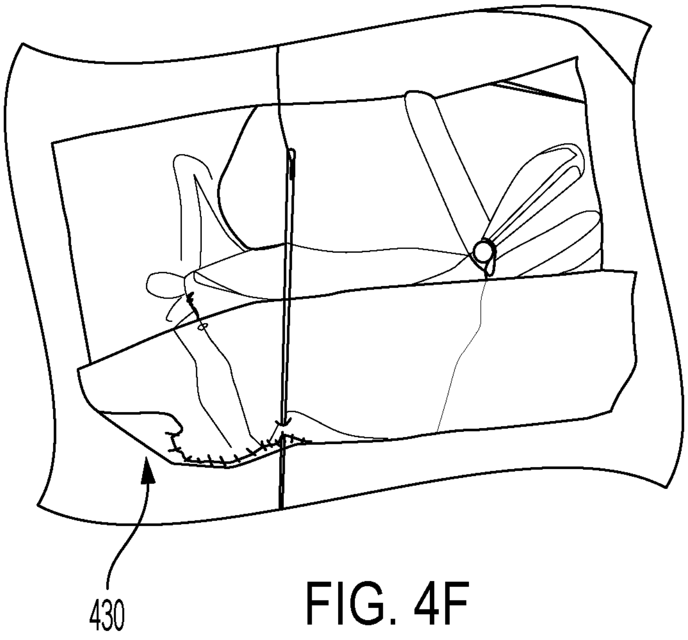
FIG. 4F is a complete tissue leaflet where the inflow skirt is in the process to be sutured from the tissue edge to margin of attachment in an exemplary embodiment.
Figure 4G:
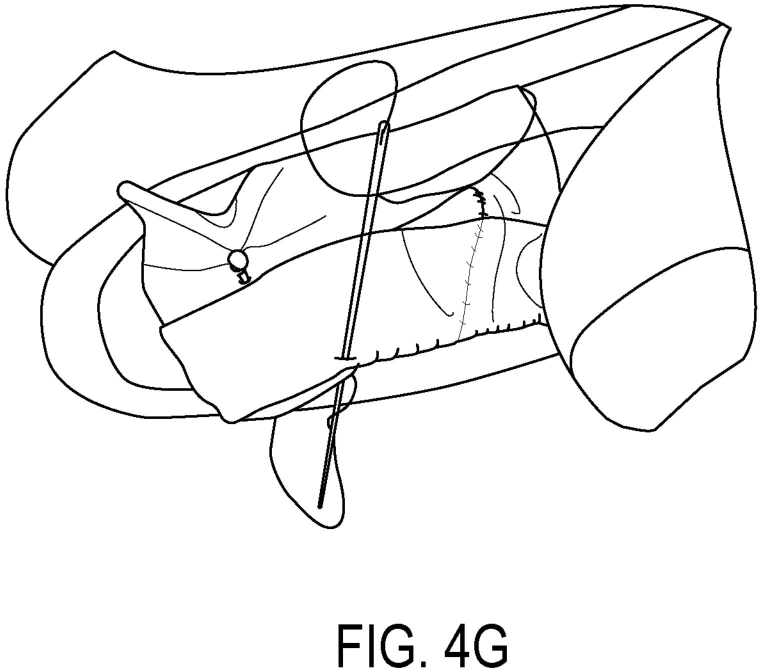
FIG. 4G is a complete tissue leaflet where the inflow skirt is being sutured and a triple lock knot following two-wrap blanket stitches is securing the inflow skirt to the margin of attachment in exemplary embodiment.

FIG. 4F illustrates sutures that can be spaced about 1 mm apart and 1 mm from the lower edge of the tissue 430. As shown in FIG. 4G, sutures can be spaced about 1 mm apart and about 1 mm from the lower edge of the tissue.

Figure 4H:
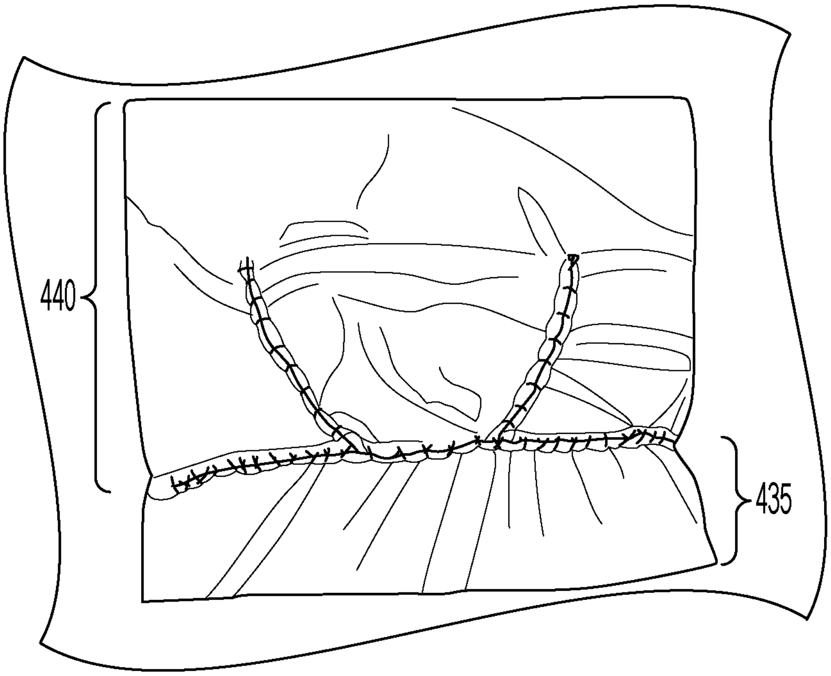
FIG. 4H is a complete tissue leaflet with the completed inflow skirt fully sutured to leaflet in an exemplary embodiment.
Figure 4I:
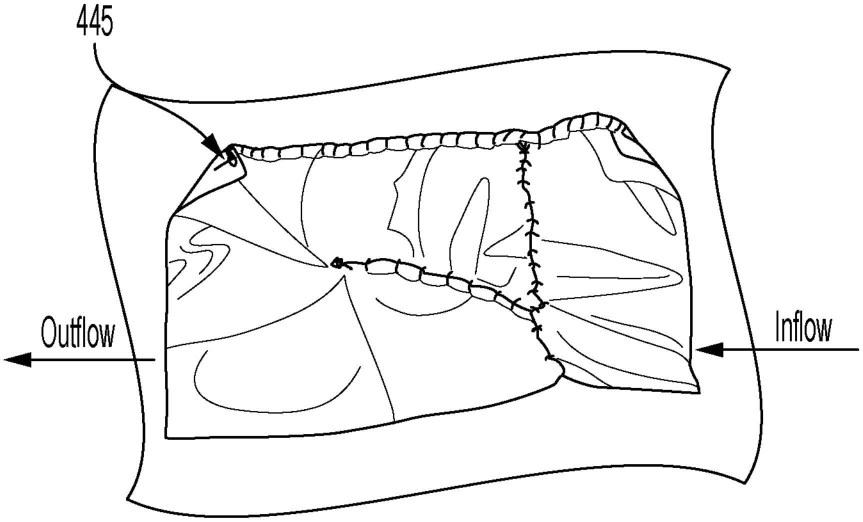

FIG. 4H shows a skirt 435 that is unfolded from the leaflet, wall, and cusp 440 is folded along the axial direction so that the cusp is on the interior of the fold. The edges of the tissue skirt/wall that will become the seam of the tissue subassembly can be aligned. Sutures can be spaced about 1 mm apart and about 1 mm from the lower edge of the tissue. As shown in FIG. 41, the stitch can be located approximately 0.5 mm from the outflow end of the tissue subassembly 445 and about 1 mm from the aligned edges of the subassembly.

Figure 5:
FIG. 5 is a side perspective of a tissue skirt according to an exemplary embodiment.

FIG. 5 shows an unattached skirt. In one aspect, the skirt is attached to the wall and leaflet skirt material. In some specific aspects, the skirt material can be made using a biological tissue from a xenogeneic source. The xenogeneic source can be selected from the group consisting of porcine, bovine, and equine. In one aspect, the xenogeneic source is porcine. In another aspect, the xenogeneic source is a xenogeneic pericardium. In another aspect, the xenogeneic source is a porcine pericardium. In one aspect, the skirt material has the same source as the monocusp leaflet. In some other aspects, the skirt material can be made using a fabric. Such fabric can include PET, PTFE fabric, ePTFE, degradable scaffold, collagen scaffold, hyaluronic scaffold, fibrin, a polymer based degradable or non-degradable material, or a biologic material. In one specific embodiment, the material has ultra-low porosity, suture retention, surface roughness, scaffold of attachment, and surface area able to attract mesenchymal cells. In one aspect, the skirt is placed on the inflow side of the valve to help with flow.

Figure 6A:
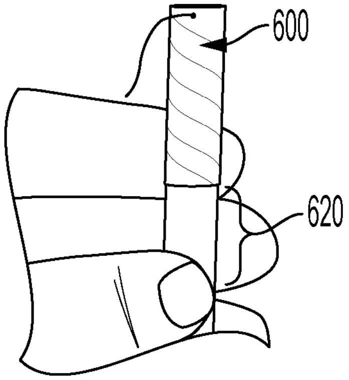
FIG. 6A is the covering for the frame wrapped around a mandrel in an exemplary embodiment.
Figure 6B:
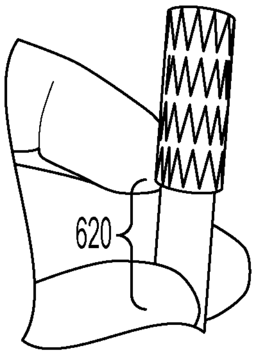
FIG. 6B is the fabric skirt covering for the frame inserted into the frame using a mandrel in an exemplary embodiment.
Figure 6C:
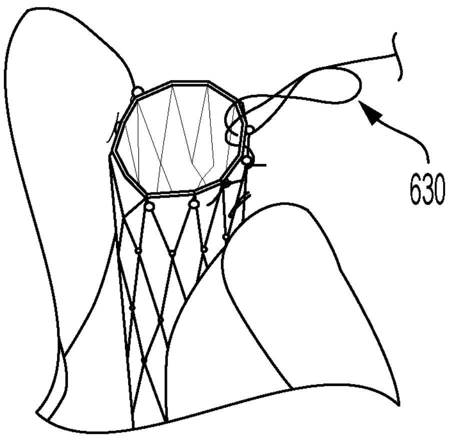
FIG. 6C is the assembled the fabric covered frame subassembly in an exemplary embodiment.

The procedure for an exemplary embodiment of the covered frame assembly is shown in FIGS. 6A, 6B, and 6C. A material for the covering for the frame assembly can include PET, PTFE fabric, ePTFE, degradable scaffold, collagen scaffold, hyaluronic scaffold, fibrin, a polymer based degradable or non-degradable material, or a biologic material. The covering for the frame is fixated to the frame. In an exemplary embodiment, a polybutester suture is used as it is strong with malleability.

FIGS. 6A, 6B, 6C shows the frame covering subassembly to be placed in the frame. In an exemplary embodiment, to assemble the device a sewing needle is prepared with polybutester, monofilament, non-absorbable surgical suture. Then, the overlapping ends of the fabric skirt can be grabbed together (e.g., between the two longer ends) so that the ends of the fabric skirt come together and the fabric skirt can be wrapped around the mandrel, identified as 620. The seam of fabric skirt can be parallel with the mandrel and the edge of the fabric skirt is extended slightly past the end of the mandrel. Then the needle is inserted inward approximately 1 mm under the free edge located on the top of the skirt. The fixation should not be too close to the edge as the fabric could tear, especially when using a suturing needle.

As shown, a knot can be made using the loose end loop, where the excess thread from the knot remains. Following that, the needle can be re-inserted into the same hole as to bring the needle to the outside, where a running stitch is made down the length of the overlap. As shown in FIG. 6A, the running stitch, identified as 600, can have about a 1 mm gap between each stitch. Once the stitches are at the bottom free edge of the skirt, thread is wrapped around the end and the needle is inserted into the backside of the last stitch made. A running stitch in the about 1 mm gaps can be created, leaving no more gaps in between each stitch leaving the stitches to appear continuous. In FIG. 6A, the stitches reach the top free edge and an end knot is created.

Shown in FIG. 6B, the frame covering is loaded around a mandrel, identified as 620, through the inner diameter of the frame. Then to fix the frame covering to the frame, a sewing needle is prepared with a temporary suture, such as PTFE. As shown in FIG. 6C, the overlap sutures are aligned on the frame covering with any eyelet in the crown, identified as 210 in FIG. 2, that corresponds and is in line to one of the frame's middle bridges. The eyelets in the crown of the frame are shown as 210 in FIG. 2. The bridges of the frame are shown at 220 in FIG. 2.

The outer diameter of the fabric skirt can be aligned with the eyelets of the frame. From here, the frame covering (fabric skirt) can be attached to the frame by inserting the needle into any eyelet that corresponds to one of the frame middle bridges. To secure the frame covering, a knot with the loose end loop shown as 630 in FIG. 6C can be used. This process can be repeated using the same thread, for the next eyelet, where a double lock stitch can be used by wrapping the loop of the previous suture around the needle twice. At the end of each suture, an end knot can be used and any excess thread can be trimmed for a completed covered frame.

Figure 7:
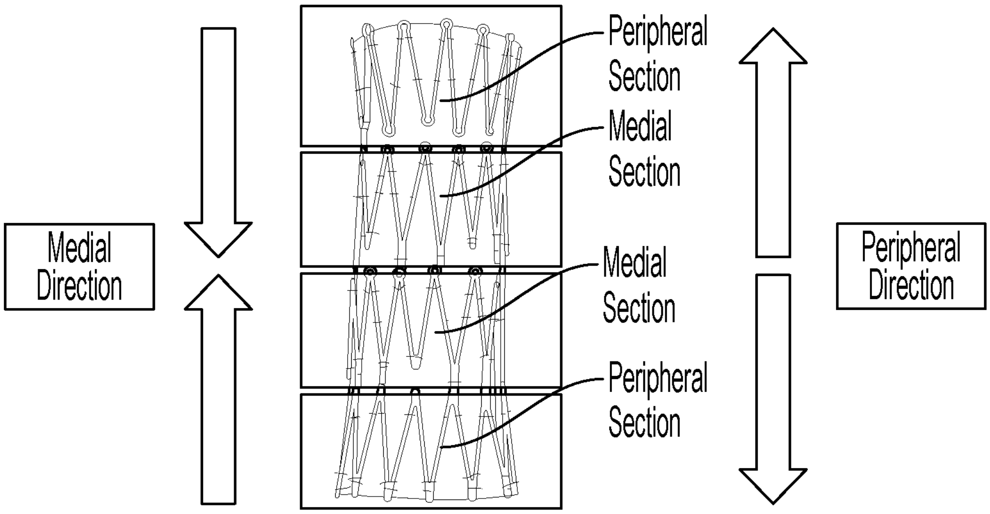
FIG. 7 is a longitudinal perspective of a valve assembly where the peripheral sections and medial sections are identified to aid final assembly in an exemplary embodiment.

FIG. 7 shows the orientation and directionality for valve assembly purposes in an exemplary embodiment. To assemble the tissue leaflet into the previously created covered frame subassembly, the tissue leaflet subassembly can be placed and inserted over a tissue insertion mandrel having a diameter of about 9 mm, 9.5 mm, 10 mm, 10.5 mm, 11 mm, 11.5 mm or 12 mm, depending on the size of valve being assembled. While assembling, it is important to ensure the tissue leaflet subassembly is centered on the mandrel and that the tissue is not damaged. Then, as seen in FIG. 8A, the tissue leaflet subassembly can be inserted on the tissue insertion mandrel 800 into the fabric skirt covered frame subassembly.

Once the tissue leaflet subassembly is inserted into the fabric skirt covered frame assembly, the assembly will have inflow and outflow directions by identifying the inflow end as the end where tissue inflow skirt is located and the outflow end as the opposite end. Following insertion of tissue, the mandrel 800 can be carefully removed, for example using forceps to ensure that edge of tissue is flush with inflow/outflow diameters of frame and wrinkles are minimized.

Figure 8A:
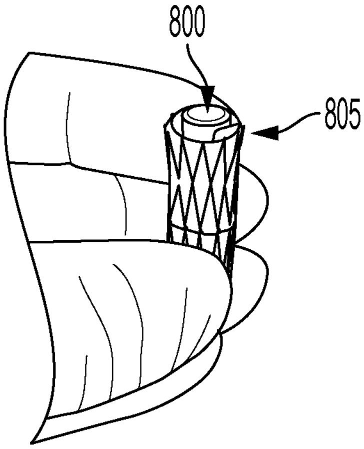
FIG. 8A is a tissue leaflet subassembly on mandrel inserted into the covered frame subassembly in an exemplary embodiment.
Figure 8B:
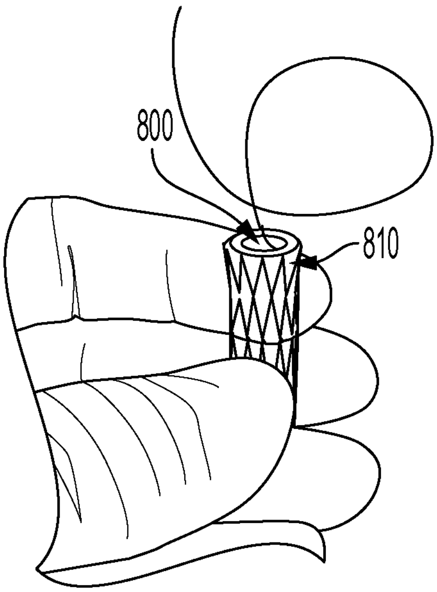
FIG. 8B is a tissue leaflet subassembly on mandrel inserted into the covered frame subassembly where the first temporary stitch at one the crown eyelets is mid-threading in an exemplary embodiment.

FIG. 8A, shows an exemplary embodiment where the sewing needle and the temporary suture, like PTFE, is used to sew into one of the frame's crown eyelets 810 and are secured. FIG. 8B is the first temporary stitch at one of the crown eyelets 810; this step can be repeated for the four other eyelets on each crown 805 of the valve assembly have a temporary knot. The temporary knots should be placed equidistantly over the twelve eyelets of each crown (inflow/outflow) of the valve assembly. A different number of eyelets can be used such as 6, 7, 8, 9, 10, 11 or 12.

Figure 9A:
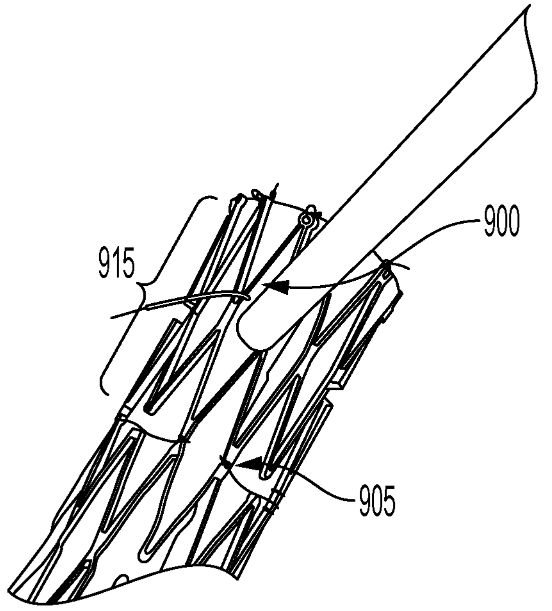
FIG. 9A is a view of the initial stitch for the transcatheter valve final assembly, where stitch is at the strut adjacent to bridge located at the peripheral side in an exemplary embodiment.
Figure 9B:
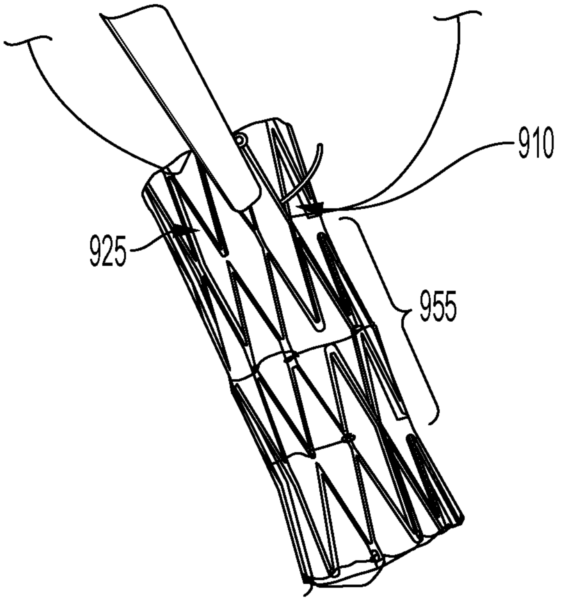
FIG. 9B is a top view of final assembly of the transcatheter valve where there is a formation of a single loop around a strut proximal to a strut bridge in an exemplary embodiment.
Figure 9C:
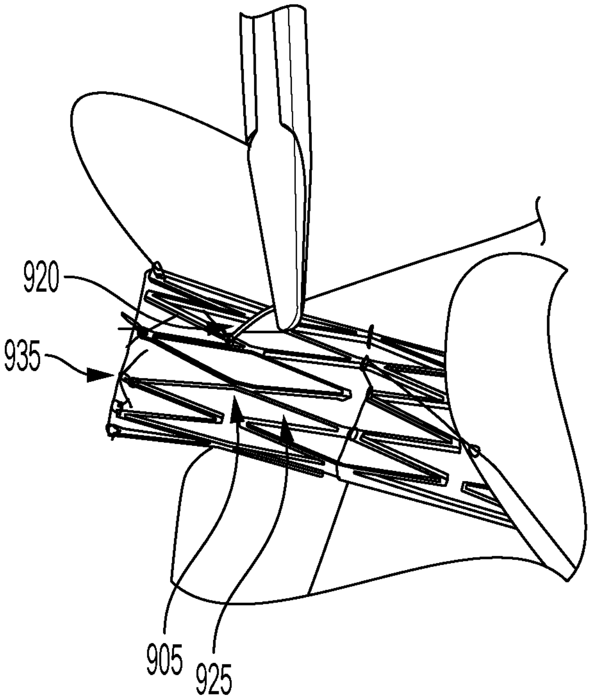
FIG. 9C is the transcatheter valve where there is re-entry of a curved needle with suture near the middle of the struts from tissue skirt interior to exterior.
Figure 9D:
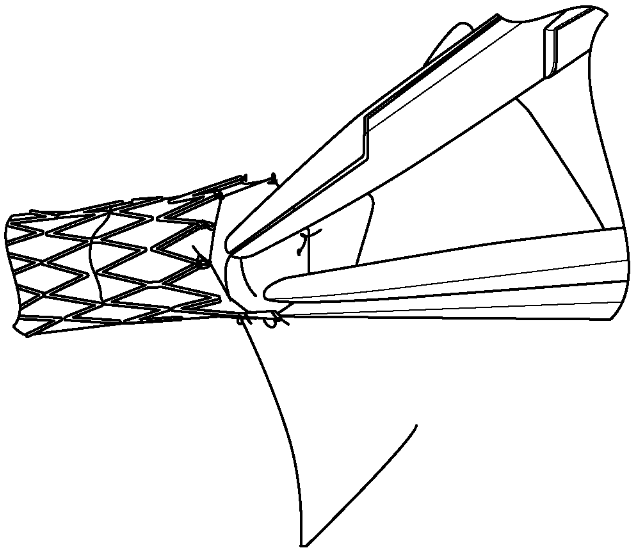
FIG. 9D is a view of final assembly of transcatheter valve where there is a re-entry of curved needle with suture near the middle of struts from tissue skirt interior to exterior in the exemplary embodiment.

In FIG. 7, the peripheral sections are shown as the flared ends of an exemplary embodiment. To attach the peripheral 915 section assembly use polybutester, monofilament, non-absorbable surgical suture with a sewing needle. As seen in FIG. 9A, begin suturing one of the peripheral 915 sections (inflow or outflow). As suturing continues, locate a bridge 905 connection and insert the needle near the bottom of the diamond strut 925 on the peripheral section. As shown in FIG. 9A, the needle should be inserted on the outside of the diamond as shown in 900. FIG. 9B shows bringing the needle through the other side of the strut at 925 at 910. As shown in FIG. 9C, a prepared sewing needle with polybutester, monofilament, non-absorbable surgical suture, seen as 920, is inserted into the first hole made. Next, the loop of the suture goes over the excess thread, the loop is pulled and the excess thread can be trimmed off As shown in FIG. 9D, from the inner side of the frame, insert the needle on the side of the strut approximately 1 mm away from the previous stitch, approximately in the middle of the strut in an exemplary embodiment. The sutures can be stitched around each strut 925 of the frame about three times. In another aspect, the sutures are stitched around each strut 925 of the frame from about one to about five times. The needle should go to the opposite side of the strut 925 that it was inserted. On the outside of the frame, the needle can be inserted into the outside of the diamond strut 925.

Figure 9E:
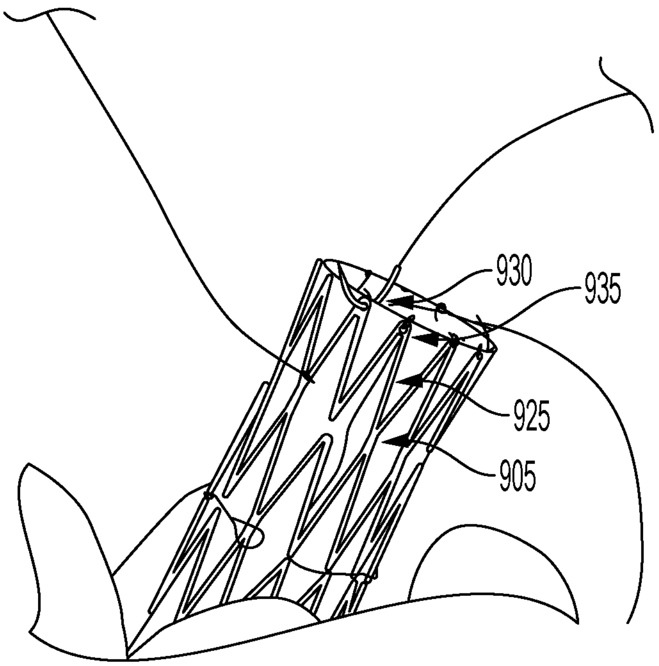
FIG. 9E is a side view of a transcatheter valve assembly where the curved needle is passed through the eyelet of crown with a suture in an exemplary embodiment.
Figure 9F:
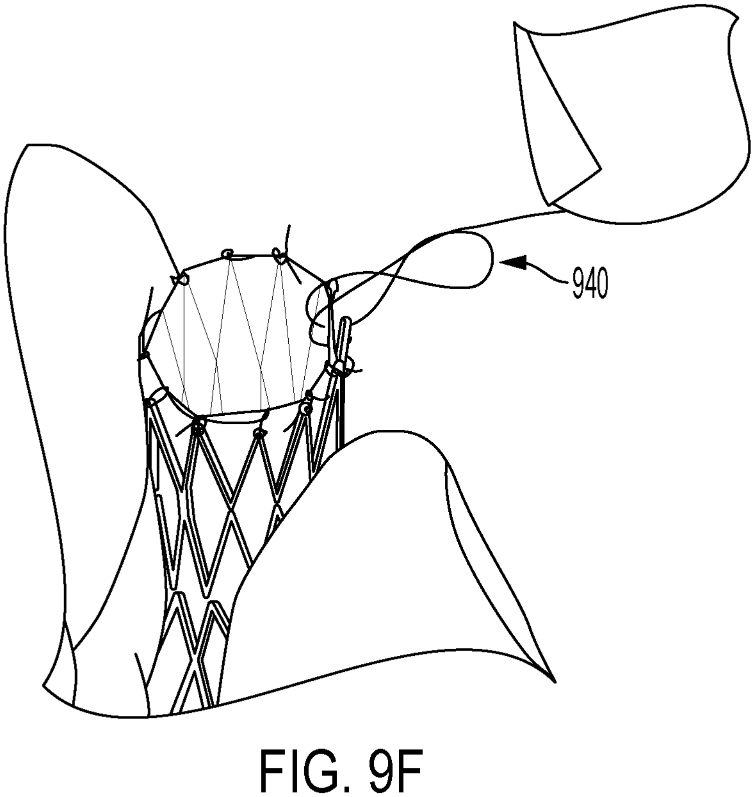
FIG. 9F is a view of a knot being tied in a transcatheter valve assembly in the eyelet in the crown in an exemplary embodiment.
Figure 9G:
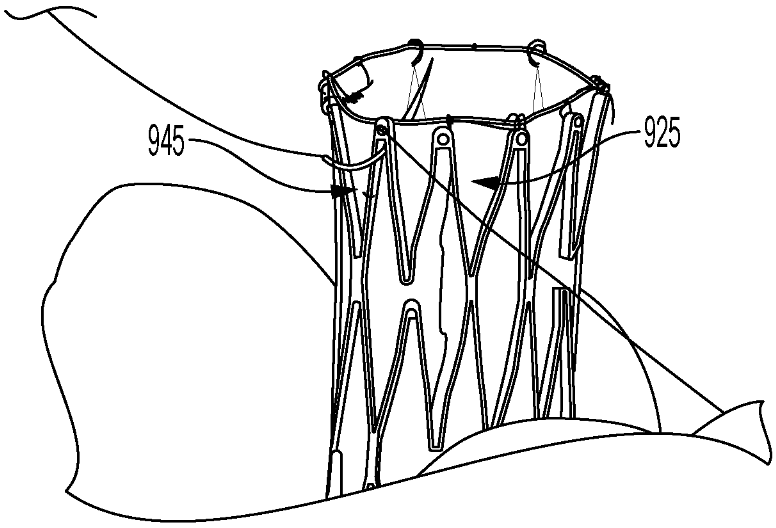
FIG. 9G is a top view of a peripheral section of the transcatheter valve assembly where the curved needle is inserted with the suture through the fabric through the middle of diamond strut in an exemplary embodiment.
Figure 9H:
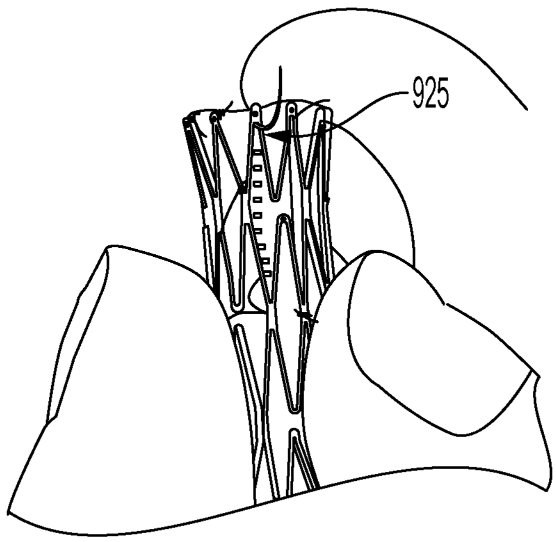
FIG. 9H is a top view of a peripheral section of the transcatheter valve assembly where the curved needle is exiting with the suture through the fabric exterior to form a loop around the strut in an exemplary embodiment.

FIG. 9E shows that another stitch can be made around the diamond strut 925 approximately 1 mm medial (away) from the last at the crown eyelet 935. Then, the curved needle can be threaded through the eyelet 935 of the crown 935 and bring the suture out, as seen in FIG. 9E at 930. As shown in FIG. 9F, a feather surgical blade can be used to remove the temporary stitch before tying a double lock-stitch knot as shown in 940. In FIG. 9G, the needle can be reinserted through the middle of the diamond strut 925 at 945. In FIG. 9H, the re-inserted curved needle can be threaded with sutures back through the interior of the tissue skirt and the needle is brought past the suture back out to the exterior and from the other side of the diamond strut 925. This is continued to match the suture pattern and configuration on both sides of the diamond strut 925.

Figure 9I:
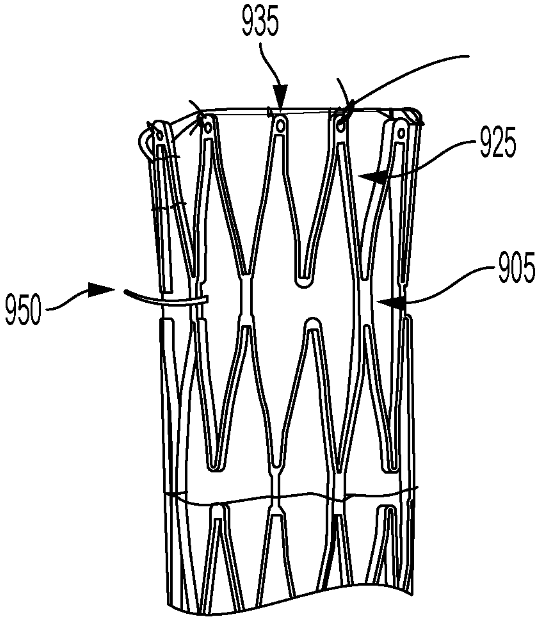
FIG. 9I is a top view of a peripheral section of the transcatheter valve assembly where the curved needle is exiting with the suture from the tissue skirt interior to exterior of fabric skirt to form a loop around the bridge in an exemplary embodiment.
Figure 9J:
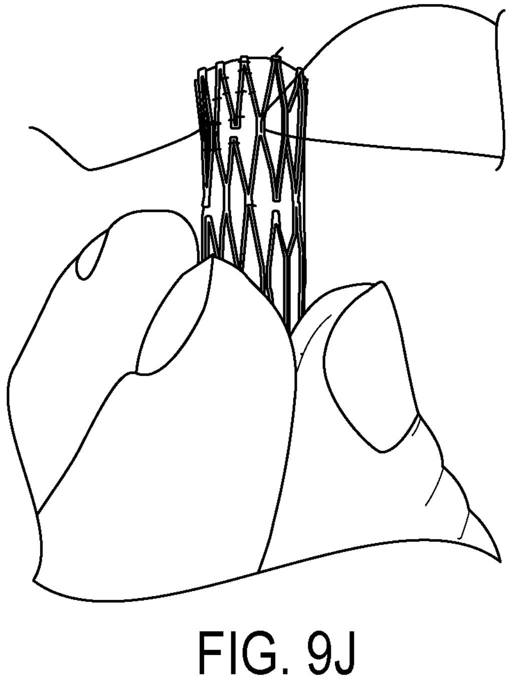
FIG. 9J is a above perspective of a final assembly of the transcatheter valve, where a loop is formed around a strut bridge with re-entry of needle and suture form exterior to interior of tissue skirt in an exemplary embodiment.

FIG. 9I shows an exemplary embodiment where the curved needled is re-inserted with suture back through the fabric skirt from the exterior to the interior of the tissue skirt. Then the needle is brought out near the strut bridge at 950. If the strut 925 being sutured has a bridge 905 connector to the adjacent section, an additional single loop stitch can be created over the bridge 905 connector. As shown in FIG. 9J, the curved needle with suture can be threaded over the bridge 905 and past the suture from exterior of fabric skirt to interior of tissue inflow skirt to form a loop around the bridge 905.

After suturing all frame 925 struts, an end knot can be created and the prior steps can be repeated for the other peripheral frame section using polybutester, monofilament, non-absorbable surgical suture and sewing needle. The needle can be inserted immediately peripheral to the strut bridge 905 on one of the medial strut sections and secure the knot. Holding the leaflet open while suturing the medial sections of the tissue leaflet will help avoid damaging the leaflet. Since there are no eyelets for the medial sections, the single loop stitch should be continued through medial struts. If the strut 925 being sutured has a bridge 905 connector to the adjacent section, an additional single loop stitch over the bridge 905 connector can be created. These steps can be repeated for the remaining struts on the medial section 955. After suturing all frame struts 925, an end knot can be created and repeat prior steps for the remaining medial frame section 955.

Figure 10:
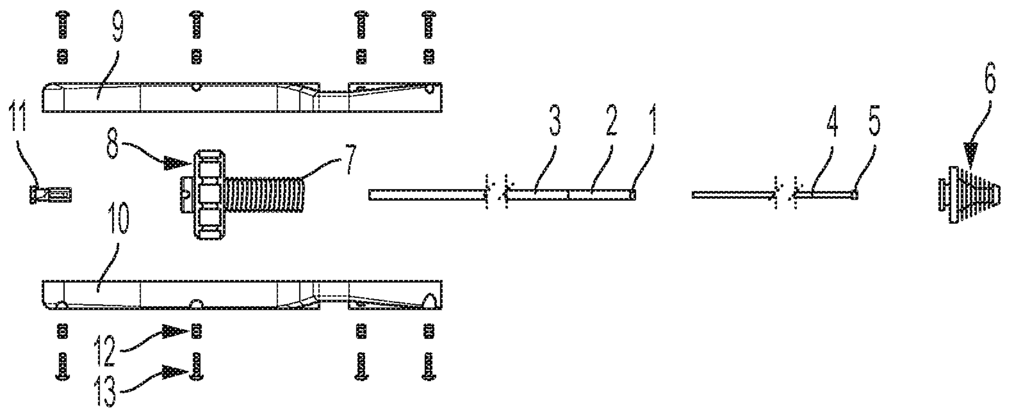
FIG. 10 is a side perspective of a disassembled delivery system according to an exemplary embodiment.

FIG. 10 shows a disassembled delivery system of where there is a capsule, catheter, pusher shaft, strain relief, lead screw, lead screw knob, handle shell (lower and upper), female connector, helical insert, BHCS, and loctite of one embodiment. In FIG. 10, there is a handle section, operational system, and catheter system has a housing area for the valve. In FIG. 10, the capsule or RO marker is identified as number 1. This indicator is the point where the valve has passed; it must be deployed and cannot be retracted back into the delivery device.

The capsule is identified as number 2. The catheter is identified as number 3; in one variation it is 0.159 in. The pusher shaft which helps deploy the valve is identified as number 4 in FIG. 10. The pusher shaft is threaded through the catheter to aid loading of the valve. The tab holder is identified as number 5 in FIG. 10. The strain relief is identified as number 6 in FIG. 10, where the lead screw is identified as number 7. The lead screw knob, identified as number 8 in FIG. 10, is where an individual can turn the mechanism to retract the pusher shaft or extend the pusher shaft. These mechanisms above are covered partially by the handle shell, which is in two parts-lower, identified as 10, and upper, identified as 9 in FIG. 10. The female connector is identified as 11 in FIG. 10. The helical insert identified as 12 in FIG. 10 is inserted into the handle shell identified as 10 in FIG. 10, where the BHCS is identified as 13 in FIG. 10 is inserted to the helical insert. The Loctite is identified as number 14 in FIG. 10.

Figure 11A:
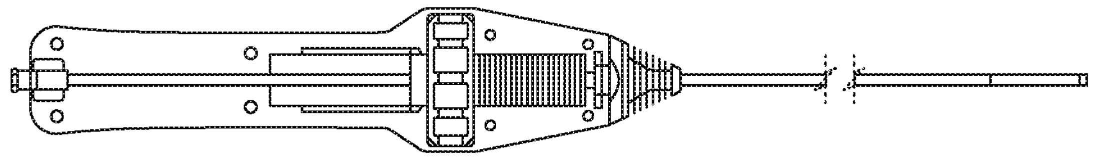
FIG. 11A is a side cut-away perspective of an assembled delivery system according to an exemplary embodiment.
Figure 11B:
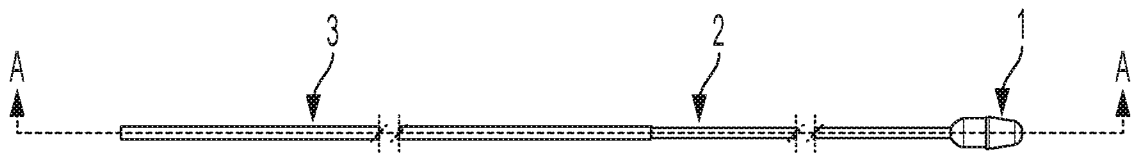
FIG. 11B is a side cut-away perspective of a nose cone assembly with inner tube assembly and sheath assembly in the delivery device in an exemplary embodiment.

FIG. 11A shows the assembled delivery system in a split view. FIG. 11B is a side cut-away perspective of a nose cone assembly with a sheath assembly that includes a nose cone as number 1 and a nose cone-braided shaft as number 2, connected to the inner tube assembly's hypotube as number 3 in the delivery device in an exemplary embodiment system. In this embodiment, the three in one system allows for the device to not separately need a dilator or introducer sheath, as the tapered bullet shape nose cone provides atraumatic entry acting as a dilator and the distal region of catheter assembly has a continuous and uniform diameter acting as an introducer sheath.

Figure 12A:
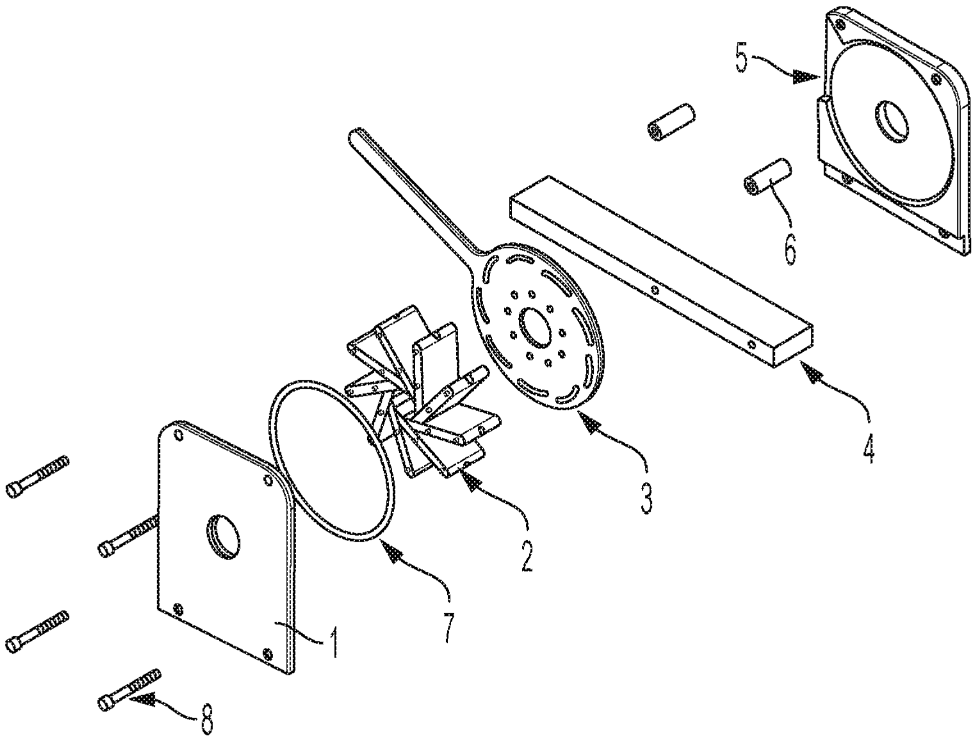
FIG. 12A is a longitudinal cut-away perspective of a crimping system (crimper) assembly according to an exemplary embodiment.
Figure 12B:
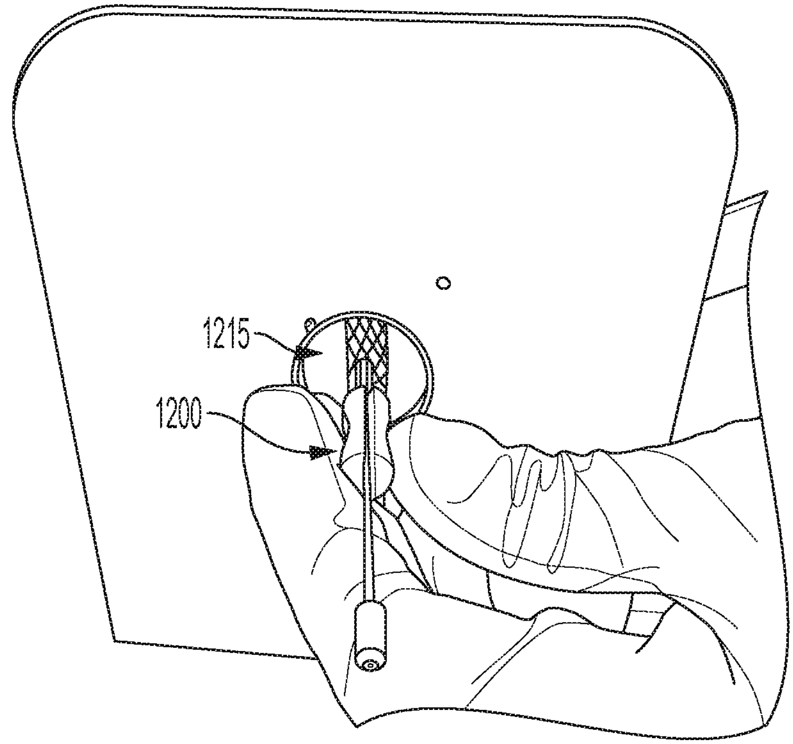
FIG. 12B is a loading of the transcatheter valve using a crimper and crimper dowel onto the delivery system in an exemplary embodiment.
Figure 12C:
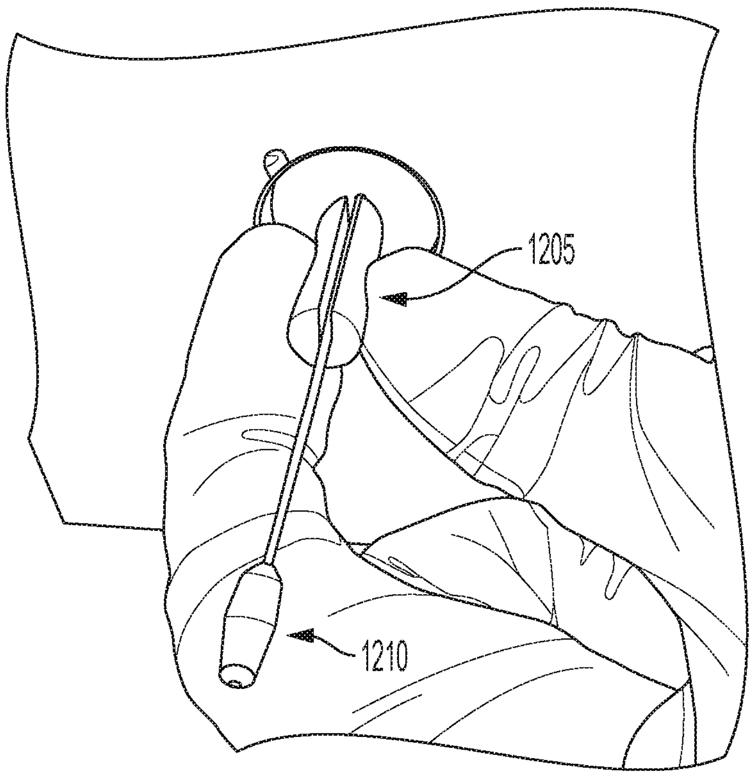
FIG. 12C is a side and slightly above perspective of a crimper compressing a transcatheter valve, where a crimper dowel is used for assistance in an exemplary embodiment.
Figure 12D:
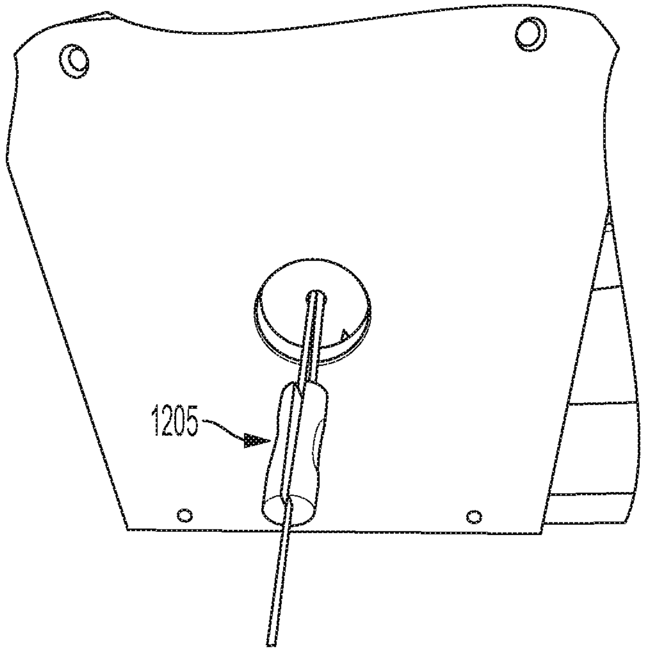
FIG. 12D is a side perspective of a crimper compressing a transcatheter valve, where a crimper dowel is used for assistance in an exemplary embodiment.
Figure 12E:
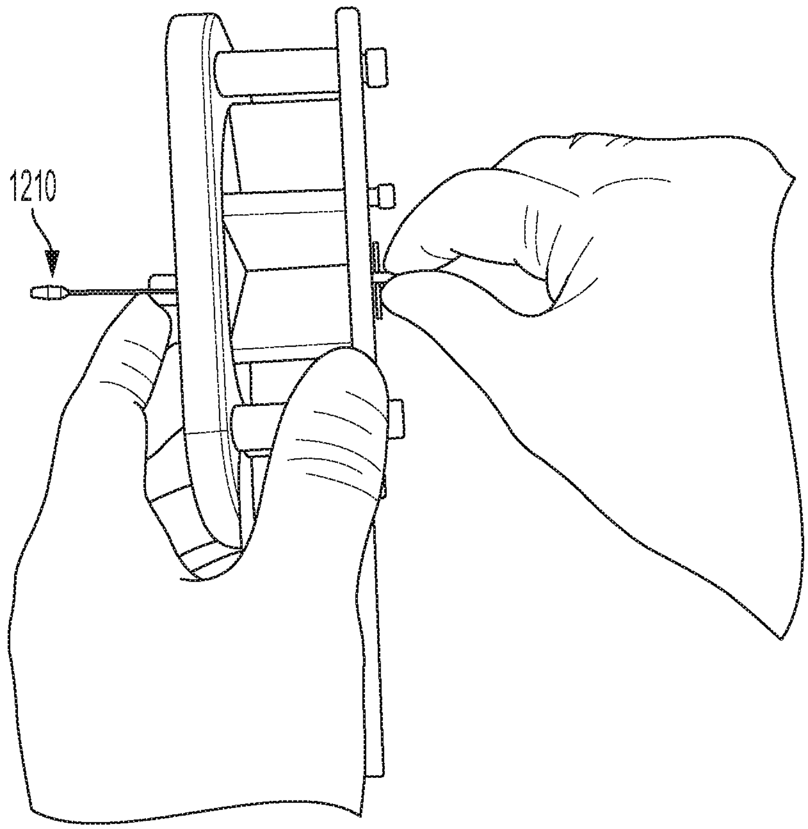
FIG. 12E is an above view of a crimper compressing a transcatheter valve, where a crimper dowel is used for assistance in an exemplary embodiment.
Figure 12F:
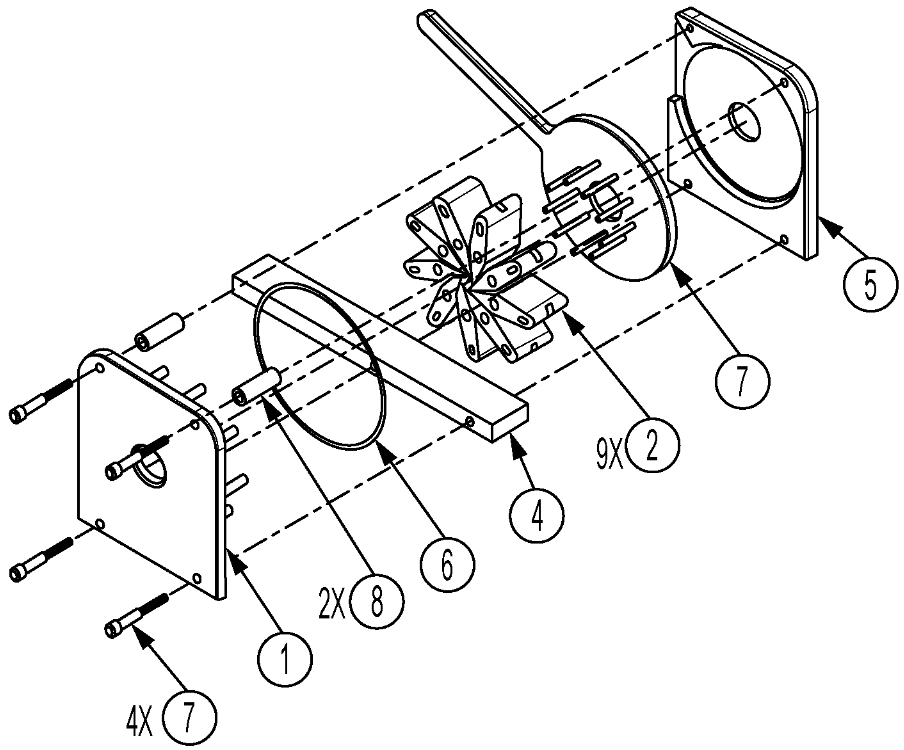
FIG. 12F is a longitudinal cut-away perspective of a crimping system (crimper) assembly according to an exemplary embodiment.
Figure 12G:
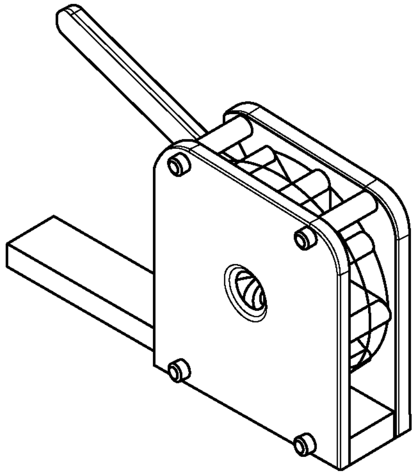
FIG. 12G is a side perspective of the crimping system (crimper) assembly according to an exemplary embodiment shown in FIG. 12F.

FIG. 12A shows a crimper where 1 is the crimper front plate, 2 is the crimper element, 3 is the crimper handle, 4 is the crimper base, 5 is the crimper back plate, 6 is the spacer for screw, 7 is the crimper element spring, and 8 is a socket head screw in an exemplary embodiment. The crimper is used to prepare the venous valve to be loaded into the delivery system. As seen in FIG. 12B, the venous valve is placed in the crimper and centered with the assistance of the crimper dowel 1205. The crimper dowel 1205 is used to assist the placement of the valve 1215 in the crimper and guide it into the delivery device 1210 as seen in FIG. 12B at 1200. FIG. 12C shows the crimper closed with the valve being held in place and pushed into the delivery device to be loaded, where the delivery device is shown as 1210. FIG. 12D shows another angle of a crimper, where the crimper dowel 1205 holds the delivery device in place. FIG. 12E shows above angle of the crimper being used to load the delivery device 1210.

Exemplary enumerated aspects of the present invention are set forth below.

1. A method of manufacturing a valve for transcatheter delivery and deployment, comprising: arranging a sheet of biological tissue in a substantially flat orientation;
   folding the sheet to form a monocusp shape having an apex and at least two margins; and
   forming a leaflet capable of placement via a catheter and operating as a valve using the monocusp shape.
2. The method of example, further comprising suturing said biological tissue to form the at least two margins of the monocusp shape.
3. The method of example, wherein the biological tissue is from a xenogeneic source.
4. The method of example, wherein the xenogeneic source is selected from the group consisting of porcine, bovine, and equine.
5. The method of example 4, wherein the xenogeneic source is porcine.
6. The method of example, wherein the xenogeneic source is pericardium.
7. The method of example, wherein the sheet is formed by cutting a contiguous biological tissue to have a shape with a top section and a bottom rectangular section.
8. The method of example, further comprising folding the top section over the bottom rectangular section to create the apex of the monocusp.
9. The method of example, further comprising suturing the top section onto the bottom rectangular section to form margins of the monocusp shape.
10. The method of example, wherein the leaflet is attached to an inflow skirt material.
11. The method of example, wherein the inflow skirt material is made using a biological tissue from a xenogeneic source.
12. The method of example, wherein the xenogeneic source is selected from the group consisting of porcine, bovine, and equine.
13. The method of example, wherein the xenogeneic source is pericardium.
14. The method of example, wherein the inflow skirt material is made using a non-biologic material.
15. The method of example, wherein the inflow skirt material has a rectangular shape.
16. The method of example, wherein the inflow skirt material has a generally rectangular shape with slightly wider end sections.
17. The method of example, wherein the valve is attached to a frame.
18. The method of example 7, wherein the leaflet is covered with a fabric skirt before suturing it to the frame.
19. The method of example, wherein the leaflet attached to the inflow skirt material is covered with a fabric skirt before suturing it to a frame.
20. The method of example, wherein the valve is a cylinder with a diameter of about 6 mm to about 18 mm.
21. The method of example, wherein the valve forms a generally cylinder shape having a diameter of about 9 mm to 12 mm.
22. A method of manufacturing a replacement valve for transcatheter delivery and deployment, comprising:
   subjecting a continuous biological tissue to a fixation treatment;
   cutting the fixated biological tissue to have a top section and a bottom section; folding the top section onto the bottom section to form an apex of a monocusp shape of a leaflet; and
   attaching the top folded section onto the bottom folded section to form a monocusp leaflet.
23. The method of example, further comprising attaching the monocusp leaflet to an inflow tissue skirt with sutures.
24. The method of example, further comprising attaching the monocusp leaflet onto a fabric skirt.

25. The method of example, wherein the biological tissue is from a xenogeneic source.
26. The method of example, wherein the xenogeneic source is selected from the group consisting of porcine, bovine, and equine.
27. The method of example 26, wherein the xenogeneic source is porcine.
28. The method of example, wherein the xenogeneic source is pericardium.
29. A replacement valve, comprising:
  a biological tissue subjected to a fixation treatment and cut to have a top section and a bottom section;
  an apex formed by folding the top section onto the bottom to form the apex of a monocusp shape of a leaflet; and
  a monocusp leaflet formed by attaching the top folded section onto the bottom folded section, the leaflet providing a spatial buffer between the monocusp and the valve wall when the valve is in the open position, and facilitating closing of the monocusp valve when adequate flow pressure gradient is created;
  a frame coupled to the monocusp leaflet.
30. The valve of example, wherein the monocusp leaflet is disposed towards one end of the frame.
31. The valve of example, wherein an inflow skirt is attached to a valve wall to minimize disruption of flow and thrombosis.
32. The valve of example, wherein the monocusp leaflet is folded from one continuous biological tissue without suturing to form the apex of the monocusp leaflet.
33. The valve of example, wherein the monocusp has a belly curve and at least one of a coalition angle of about 20 degrees to 80 degrees, a free margin angle between commissure points of about 90 degrees to 20 degrees, a leaflet total height of about 6 mm to 11 mm a coaptation height ratio of about 0.5-1, a commissure-to-commissure (CC)/flat width of about 12 mm-20 mm, a coaptation gap of about 0 to 3 mm, and a free margin distance of about 14 mm-27 mm.
34. The valve of example, wherein the wall is attached to the leaflet.
35. An implantable compressible vein frame, comprising:
  a first section formed from a first plurality of segments;
  a second section connected to the first section, the second section formed from a second plurality of segments, wherein the connected first section and second section form a hollow cylinder; and
  wherein the first plurality of segments includes a first plurality of proximal peaks and a first plurality of distal peaks and the second plurality of segments includes a second plurality of proximal peaks and a second plurality of distal peaks.
36. The vein frame of example 35, wherein each end of the cylinder has a flare between about 0 mm to about 10 mm from the beginning of the flare to the end of the flare and wherein the hollow cylinder is compressible to 12Fr-16Fr.
37. The vein frame of example 35, wherein each end of the cylinder has a flare that anchors or hooks the frame to the natural tissue upon insertion.
38. The vein frame of example, further comprising a third body section connected to the second section, the third section formed from a third plurality of segments, wherein the connected second section and third section form a hollow cylinder; and
  wherein the second plurality of segments includes a third plurality of proximal peaks and a second plurality of distal peaks and the third plurality of segments includes a third plurality of proximal peaks and a second plurality of distal peaks.
39. The vein frame of example 38, further comprising a fourth body section connected to the third section, the fourth section formed from a fourth plurality of segments, wherein the connected third section and fourth section form a hollow cylinder; and
  wherein the third plurality of segments includes a fourth plurality of proximal peaks and a third plurality of distal peaks, and the fourth plurality of segments includes a third plurality of proximal peaks and a second plurality of distal peaks.
40. The vein frame of example, further comprising two to sixteen crowns formed on each of the first section and the second section to aid compressibility.
41. The vein frame of example 40, further comprising anchors or hooks along the cylinder and at the crowns.
42. The vein frame of example 40, wherein a radial strength can be 17-20 N, depending on the number of sections and crowns.
43. The vein frame of example, wherein the first section and section are self-expanding or assisted with a balloon inflation system.
44. The vein frame of example, wherein the first section and second section are covered with a material including a fabric or coating.
45. A method of manufacturing an implantable compressible vein frame, comprising:
  forming a first section from a first plurality of segments;
  forming a second section connected to the first section, the second section formed from a second plurality of segments, wherein the connected first section and second section form a hollow cylinder, each end of the cylinder being flared;
  wherein the first plurality of segments includes a first plurality of proximal peaks and a first plurality of distal peaks, and the second plurality of segments includes a second plurality of proximal peaks and a second plurality of distal peaks providing stability and able to compress the structure;
46. The method of example 45, further comprising forming a third body section connected to the second section, the third section formed from a third plurality of segments, wherein the connected second section and third section form a hollow cylinder; and
  wherein the second plurality of segments includes a third plurality of proximal peaks and a second plurality of distal peaks, and the third plurality of segments includes a third plurality of proximal peaks and a second plurality of distal peaks.
47. The method of example 45, further comprising forming a fourth body section connected to the third section, the fourth section formed from a fourth plurality of segments, wherein the connected third section and fourth section form a hollow cylinder; and
  wherein the third plurality of segments includes a fourth plurality of proximal peaks and a third plurality of distal peaks and the fourth plurality of segments includes a third plurality of proximal peaks and a second plurality of distal peaks.
48. The method of example 45, further, comprising placing a replacement valve leaflet within the first and second sections, the replacement valve leaflet including a leaflet, a wall, and an inflow skirt.

49. A crimping device, comprising:
   a crimper front plate;
   a crimper element coupled to the crimper front plate; and
   a crimper handle coupled to the crimper element, wherein the crimper element is adapted to receive a compressible vein frame for transcatheter delivery of the frame into a vein.
50. The device of example 49, wherein the device compresses the compressible vein frame into a cylindrical shape.
51. The device of example 49, further comprising a non-blood contacting device with crimping dowel operable with the crimper element, wherein the dowel is pushed through the crimper element to guide the compressible vein frame while maintaining the crimped state.
52. A delivery system, comprising: at least an inner tube assembly; a sheath assembly coupled to the inner tube assembly; a movable catheter assembly operable with the sheath assembly; and a handle, wherein the catheter assembly is adapted to receive a compressible vein frame for transcatheter delivery of the frame into a vein.
53. The device of example 52 wherein the sheath assembly is connected to the inner tube assembly by having the hypotube of the inner tube assembly cover the nose cone-braided shaft of the sheath assembly partially or completely, and wherein the sheath assembly and inner tube assembly are capable of having a standard guidewire pass through.
54. The device of example 53, wherein the catheter assembly is slidably placed over the sheath assembly, and includes a proximal region and a distal region.
55. The device of example 54, wherein one end of a proximal region of the catheter assembly is connected to the handle and a second end of the proximal region of the catheter assembly is connected to the distal region of the catheter assembly, and wherein the one end of the distal region of the catheter assembly can be configured to compressively contain the transcatheter valve in a compressed arrangement and the second end of the distal region of the catheter assembly is connected to the proximal region of the catheter assembly.
56. The device of example 55, wherein the handle is configured to controllably move the catheter assembly relative to the sheath assembly.
57. The device of example 55, wherein controllably moving the handle provides a resting state in which a distal region of the catheter assembly is closer to a nose cone or a delivery state in which the distal region of the catheter assembly is pulled away from a nose cone.
58. A crimping device, comprising:
   a crimper front plate;
   a crimper element coupled to the crimper front plate;
   a crimper handle coupled to the crimper element, wherein the crimper element is adapted to receive a compressible vein frame for transcatheter delivery of the frame into a vein; and a guiding dowel operable with the crimper element to assist loading the crimper with a transcatheter device.
59. The device of example 58, wherein the guiding dowel has a wider base to be gripped and narrows to thinly fit within the crimping element.
60. The device of example 58, wherein the guiding dowel allows for a nose cone of the transcatheter device to be threaded through.
61. The device of example 60, wherein the guiding dowel is pushed to guide the transcatheter device to be threaded while maintaining the transcatheter in a crimped state.
62. A delivery system, comprising:
   a first assembly including a catheter, a capsule, a handle top and bottom shell, a pusher shaft, a tab holder, an indication maker, a main screw knob, and a lead screw;
   a second assembly coupled to the first assembly including a delivery system flushing accessories and a nose cone assembly, wherein there is a single diameter for the entire distal end of first assembly and the distal end of second assembly.
63. The delivery system of example 62, wherein the first assembly includes a tab holder at the end of a pusher shaft to firmly hold the bottom of a device within the first assembly and aid in releasing/deploying the device during implantation while the pusher shaft maintains column strength.
64. The delivery system of example 63, wherein the pusher shaft has a reduced diameter in a middle portion to prevent kinking and to avoid friction during operation.
65. The delivery system of example 62, further comprising a guiding dowel operable with the first assembly and the second assembly to push a transcatheter device through a crimper to guide the transcatheter device while maintaining the transcatheter device in a crimped state.
66. The delivery system of example 62, wherein the nose cone assembly and/or distal end of the catheter includes an indication marker (radiopaque (RO) marker) that can be visualized through fluoroscopy.

What is claimed is:

1. A method of manufacturing a replacement venous valve for transcatheter delivery and deployment, comprising:
   cutting a planar and fixated sheet of biological tissue to have a top section and a bottom rectangular section, wherein the top section is cut to resemble the shape of a single cusp having a belly curve;
   folding the top section over the bottom rectangular section to form an apex of a monocusp shape of a leaflet;
   suturing the top section onto the bottom rectangular section to form margins of the monocusp shape; and
   rolling opposite lateral edges of the rectangular section into a generally cylindrical shape to form a monocusp leaflet of a replacement venous valve capable of placement via a catheter and operating as a monocusp valve using the monocusp shape.

2. The method of claim 1, further comprising attaching the monocusp leaflet to an inflow skirt with sutures.

3. The method of claim 2, wherein the inflow skirt is attached to the monocusp leaflet on the in-flow side of the monocusp leaflet.

4. The method of claim 2, wherein the inflow skirt is made using a biological tissue from a xenogeneic source.

5. The method of claim 4, wherein the xenogeneic source is selected from the group consisting of porcine, bovine, and equine.

6. The method of claim 4, wherein the xenogeneic source is pericardium.

7. The method of claim 2, wherein the inflow skirt is made using a fabric.

8. The method of claim 2, wherein the inflow skirt has a rectangular shape.

9. The method of claim 2, wherein the inflow skirt has a generally rectangular shape with slightly wider end sections.

10. The method of claim 2, further comprising covering the monocusp leaflet attached to the inflow skirt with a fabric skirt; and attaching the covered monocusp leaflet to a frame.

11. The method of claim 1, further comprising attaching the monocusp leaflet to a fabric skirt.

12. The method of claim 1, wherein the biological tissue is from a xenogeneic source.

13. The method of claim 12, wherein the xenogeneic source is selected from the group consisting of porcine, bovine, and equine.

14. The method of claim 12, wherein the xenogeneic source is porcine.

15. The method of claim 12, wherein the xenogeneic source is pericardium.

16. The method of claim 1, further comprising attaching the monocusp leaflet to a frame with sutures.

17. The method of claim 16, wherein the monocusp leaflet is attached to the frame such that the monocusp leaflet partially covers a circumference of the frame.

18. The method of claim 16, wherein the monocusp leaflet is attached to the frame such that the monocusp leaflet fully covers a circumference of the frame.

19. The method of claim 16, wherein the monocusp leaflet is attached to a fabric skirt before attaching the monocusp leaflet to the frame.

20. The method of claim 19, wherein the fabric skirt is made using a material that has at least one of ultra-low profile, adequate porosity and suture retention, surface roughness, scaffold for cell attachment, and surface area able to attract migrated native cells to promote tissue ingrowth for improved device sealing, and long-term device migration resistance post-implantation.

21. The method of claim 19, wherein the fabric skirt is made using a synthetic or natural material.

22. The method of claim 16, wherein the frame is expandable and compressible.

23. The method of claim 1, wherein the generally cylindrical shape of the replacement venous valve has a diameter of about 6 mm to about 18 mm.

24. The method of claim 1, wherein the generally cylindrical shape of the replacement venous valve has a diameter of about 9 mm to 12 mm.

25. The method of claim 1, wherein the monocusp leaflet provides a spatial buffer between the monocusp and a valve wall of the replacement venous valve when the replacement venous valve is in the open position, and facilitates closing of the replacement venous valve when adequate flow pressure gradient is created.

26. The method of claim 1, wherein the monocusp leaflet has at least one of a coaptation angle of about 20 degrees to 80 degrees, a free margin angle between commissure points of about 90 degrees to 270 degrees, a monocusp leaflet total height of about 6 mm to 11 mm, a coaptation height ratio of about 0.5 to 1, a commissure-to-commissure (CC)/flat width of about 12 mm to 20 mm, a coaptation gap of about 0 to 3 mm, and a free margin distance of about 14 mm to 27 mm.

27. The method of claim 1, wherein the monocusp leaflet has at least one of a coaptation angle of about 30 degrees to 65 degrees, a free margin angle between commissure points of about 110 degrees to 130 degrees, a monocusp leaflet total height of about 7 mm to 10 mm, a coaptation height ratio of about 0.85 to 095, a commissure-to-commissure (CC)/flat width of about 16 mm to 18 mm, a coaptation gap of about 0 to 2 mm, and a free margin distance of about 17 mm to 22 mm.

* * * * *